United States Patent
Wu et al.

(10) Patent No.: US 10,278,217 B2
(45) Date of Patent: Apr. 30, 2019

(54) MANAGING DYNAMIC CONNECTION INTERVALS FOR IMPLANTABLE AND EXTERNAL DEVICES

(71) Applicant: Pacesetter, Inc., Sunnyvale, CA (US)

(72) Inventors: Yongjian Wu, Saratoga, CA (US); Chao-Wen Young, Cupertino, CA (US); Jun Yang, Valencia, CA (US); Xing Pei, Thousand Oaks, CA (US); Reza Shahandeh, Thousand Oaks, CA (US)

(73) Assignee: Pacesetter, Inc., Sunnyvale, CA (US)

( * ) Notice: Subject to any disclaimer, the term of this patent is extended or adjusted under 35 U.S.C. 154(b) by 0 days.

(21) Appl. No.: 15/676,571

(22) Filed: Aug. 14, 2017

(65) Prior Publication Data

US 2018/0152972 A1    May 31, 2018

Related U.S. Application Data

(60) Provisional application No. 62/427,216, filed on Nov. 29, 2016.

(51) Int. Cl.
| | |
|---|---|
| *H04W 4/80* | (2018.01) |
| *A61N 1/372* | (2006.01) |
| *H04L 29/06* | (2006.01) |
| *H04W 52/02* | (2009.01) |
| *H04W 76/10* | (2018.01) |
| *H04W 76/20* | (2018.01) |

(52) U.S. Cl.
CPC ........ *H04W 76/10* (2018.02); *A61N 1/37223* (2013.01); *A61N 1/37247* (2013.01); *A61N 1/37276* (2013.01); *H04L 69/28* (2013.01); *H04W 4/80* (2018.02); *H04W 52/0216* (2013.01); *H04W 76/20* (2018.02); *H04W 52/0254* (2013.01); *H04W 52/0277* (2013.01); *Y02D 70/00* (2018.01); *Y02D 70/10* (2018.01); *Y02D 70/14* (2018.01); *Y02D 70/144* (2018.01); *Y02D 70/164* (2018.01); *Y02D 70/20* (2018.01); *Y02D 70/26* (2018.01)

(58) Field of Classification Search
CPC ........ H04W 76/20; H04W 4/80; H04W 76/10
See application file for complete search history.

(56) References Cited

U.S. PATENT DOCUMENTS

| | | |
|---|---|---|
| 9,072,913 B2 | 7/2015 | Jacobson |
| 9,168,383 B2 | 10/2015 | Jacobson et al. |
| 2012/0101544 A1* | 4/2012 | Hoberman ........... A61N 1/3718 607/28 |

(Continued)

OTHER PUBLICATIONS

Application filed Mar. 29, 2016; U.S. Appl. No. 15/084,373.

*Primary Examiner* — Diane D Mizrahi
(74) *Attorney, Agent, or Firm* — Theresa A. Raymer

(57) ABSTRACT

A method, system and external instrument are provided. The method initiates a communication link between an external instrument (EI) and an implantable medical device (IMD), established a first connection interval for conveying data packets between the EI and IMD and monitors a connection criteria that includes at least one of a data throughput requirement. A battery indicator or link condition of the communications link is between the IMD and EI. The method further changes from the first connection interval to a second connection interval based on the connection criteria.

15 Claims, 9 Drawing Sheets

(56) References Cited

U.S. PATENT DOCUMENTS

| | | | |
|---|---|---|---|
| 2013/0165819 A1* | 6/2013 | Tieu | A61N 1/37276 |
| | | | 600/595 |
| 2015/0148868 A1 | 5/2015 | Shahandeh et al. | |
| 2015/0255858 A1* | 9/2015 | Li | H01Q 1/273 |
| | | | 343/702 |
| 2017/0309166 A1* | 10/2017 | Abrahamson | A61N 1/37223 |
| 2018/0078777 A1* | 3/2018 | Wu | A61N 1/37252 |
| 2018/0288147 A1* | 10/2018 | Shanmugam | H04L 67/1095 |

* cited by examiner

MANAGING DYNAMIC CONNECTION INTERVALS FOR IMPLANTABLE AND EXTERNAL DEVICES

PRIORITY CLAIM

The present application relates to and claims priority from U.S. provisional application Ser. No. 62/427,216, filed Nov. 29, 2016, entitled "MANAGING DYNAMIC CONNECTION INTERVALS FOR IMPLANTABLE AND EXTERNAL DEVICES," which is hereby expressly incorporated by reference in its entirety to provide continuity of disclosure.

BACKGROUND

Embodiments of the present disclosure generally relate to systems and methods for establishing a communication link between devices, and more particularly to managing dynamic connection intervals for BLE utilized to establish communication links between implantable medical devices and external instruments.

An implantable medical device (IMD) is a medical device to be implantable within a patient anatomy. Some IMDs employ one or more leads with electrodes that either receive or deliver voltage, current or other electromagnetic pulses from or to an organ or tissue for diagnostic or therapeutic purposes. Other IMDs operate without separate leads, and may be referred to as leadless IMDs. In general, IMDs include a battery, electronic circuitry, a pulse generator, a transceiver and/or a microprocessor that is configured to handle communication with an external instrument as well as control patient therapy. The components of the IMD are hermetically sealed within a metal housing.

IMDs are programmed by, and exchange data with, external instruments (EI) controlled by physicians and/or the patient. The external instruments use commercial operating systems (e.g., iOS, Android) that communicate through wireless bi-directional communication links with the IMDs. The bi-direction communication link is formed based on advertisement notices received by the external instruments. The advertisement notices are broadcast by the IMD at a predetermined constant frequency based on the wireless protocol. However, the current drain expended by the IMD to broadcast the advertisement notices can be too high where battery life is a concern, particularly in smaller devices that have limited space for batteries. To conserve current drain, it has been proposed to transmit advertisement notices at a lower frequency than defined by the wireless protocol, such as by waiting several seconds or minutes between transmission of successive advertisement notices (e.g., instead of a few seconds or milliseconds).

However, many external instruments have built in constraints related to how long the external instrument will monitor for advertisement notices for usability and power consumption purposes. If an advertisement notice is not received by the external instrument within a predetermined number of monitoring periods, the external instrument may decrease the frequency of the monitoring period. If the external instrument misses an advertisement notice, minutes may pass before the external instrument begins to monitor for an advertisement notice. When multiple unsuccessful monitoring periods occur, the battery of the external instrument is undesirably drained.

Further, many external instruments (EIs) use Bluetooth Low Energy (BLE) to connect to an IMD. The power consumption of the battery of an IMD is a major design constraint. There is a limited total amount of drain allowable for active device communications with EIs when the BLE link is active. While in an active connection, the BLE specification defines the connection interval to be the interval between two consecutive connection events (a data exchange before going back to an idle state to save power), and this connection interval can be set to a value between 7.5 ms and 4 s.

If the BLE link utilizes a protocol with connection interval 1, such as a 20 ms per packet exchange, a good data throughput is likely due to more data being exchanged during a fixed time period. However, the power consumption during the connection interval 1 will be higher during the session in which the EI is connected. Conversely, if the BLE link utilizes connection interval 2, such as a 100 ms per packet exchange, a limited data throughput bandwidth is likely due to limited data being exchanged during a fixed time period. However, the decreased power consumption during the connection interval 2 is desired and is beneficial for the longevity of the IMD. In accordance with the foregoing, conventional BLE telemetry protocols cause an undue drain on the IMD battery. A need exists for improved methods and systems to manage the connection interval of a BLE link between an EI and an IMD.

BRIEF SUMMARY

In accordance with embodiments herein a method is provided. The method initiates a communication link between an external instrument (EI) and an implantable medical device (IMD), established a first connection interval for conveying data packets between the EI and IMD and monitors a connection criteria that includes at least one of a data throughput requirement. A battery indicator or link condition of the communications link is between the IMD and EI. The method further changes from the first connection interval to a second connection interval based on the connection criteria.

Optionally, the changing operation may dynamically change between the first and second connection intervals based on the data throughput requirements. The changing operation may dynamically change between the first and second connection intervals based on the link condition of the communications link. The second connection interval may be longer than the first connection interval. The changing operation may comprises changing to the second connection interval when the data throughput requirement drops below a data threshold. The first connection interval may be shorter than the second connection interval. The method may further comprise changing from the second connection interval back to the first connection interval when the link condition drops below a quality threshold.

Optionally, the method may upload device configuration information from the IMD to the EI utilizing the first connection interval and may conveying control commands between the IMD and EI utilizing the second connection interval. The changing operation may further comprise conveying an interval command from the EI to the IMD directing the IMD to change to the second connection interval. The changing operation may further comprise selecting one of the first and second connection intervals to maintain a current drain on a battery of the IMD within a predetermined current drain limit.

In accordance with embodiments herein, a system for establishing a bi-directional communication link is provided. The systems comprises an implantable medical device (IMD) having a sensing circuit to collect sensed data. The IMD includes a radio frequency (RF) circuit and a memory. An external instrument (EI) is provided having one or more processors electrically coupled to an RF circuit and a memory. The one or more processors are configured to initiate a communication link between the EI and the IMD, establish a first connection interval for conveying data packets between the EI and IMD, monitor a connection criteria that includes at least one of a data throughput requirement, a battery indicator or link condition of the communications link between the IMD and EI and change from the first connection interval to a second connection interval based on the connection criteria.

Optionally, the one or more processors may dynamically change between the first and second connection intervals based on the link condition of the communications link. The second connection interval may be longer than the first connection interval. The one or more processors may change to the second connection interval when the data throughput requirement drops below a data threshold. The first connection interval may be shorter than the second connection interval. The one or more processors may change from the second connection interval back to the first connection interval when the link condition drops below a quality threshold. The first and second connection intervals may represent first and second amounts of time between starting times of successive connection events. The one or more processors may change between first and second connection interval schemes based on the connection criteria. The first and second connection interval schemes may be defined based on at least one of slave latency or supervision timeout.

In accordance with embodiments herein, an external instrument (EI) for establishing a bi-directional communication link with an implantable medical device (IMD) is provided. The EI has a sensing circuit to collect sensed data. The IMD includes a radio frequency (RF) circuit and a memory. The EI comprises an RF circuit, memory storing program instructions, and one or more processors electrically coupled to the RF circuit. The one or more processors, when executing the program instructions initiates a communication link between the EI and the IMD, establishes a first connection interval for conveying data packets between the EI and IMD, monitors a connection criteria that includes at least one of a data throughput requirement, a battery indicator or link condition of the communications link between the IMD and EI and changes from the first connection interval to a second connection interval based on the connection criteria.

Optionally, the one or more processors may dynamically change between the first and second connection intervals based on the link condition of the communications link. The second connection interval may be longer than the first connection interval. The one or more processors may change to the second connection interval when the data throughput requirement drops below a data threshold. The first connection interval may be shorter than the second connection interval. The one or more processors may change from the second connection interval back to the first connection interval when the link condition drops below a quality threshold. The first and second connection intervals may represent first and second amounts of time between starting times of successive connection events.

DETAILED DESCRIPTION

Figure 1:
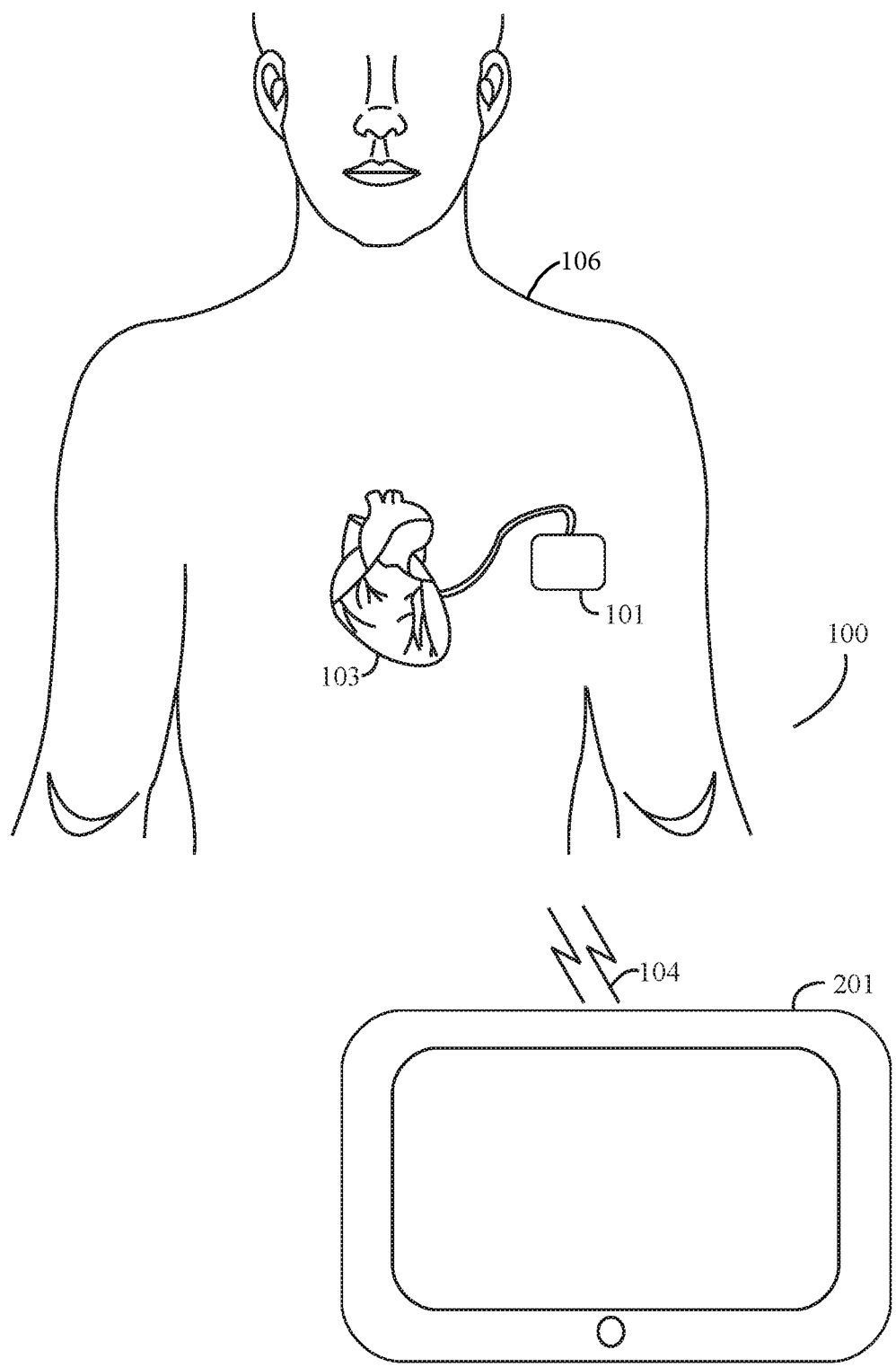
FIG. 1 illustrates a simplified block diagram of a system for initiating a bi-directional communication link in accordance with embodiments herein.

It will be readily understood that the components of the embodiments as generally described and illustrated in the figures herein, may be arranged and designed in a wide variety of different configurations in addition to the described example embodiments. Thus, the following more detailed description of the example embodiments, as represented in the figures, is not intended to limit the scope of the embodiments as claimed, but is merely representative of example embodiments.

Reference throughout this specification to "one embodiment" or "an embodiment" (or the like) means that a particular feature, structure, or characteristic described in connection with the embodiment is included in at least one embodiment. Thus, appearances of the phrases "in one embodiment" or "in an embodiment" or the like in various places throughout this specification are not necessarily all referring to the same embodiment.

A connection interval scheme may be defined based on various connection parameters, such as connection interval, slave latency, supervision timeout and the like.

The term "connection interval" refers to an amount of time between starting times of successive connection events. The connection interval is an amount of time between successive connection events. For example, in accordance with some BLE communications protocols, the connection interval may be a multiple of 1.25 ms in the range of 7.5 ms to 4.0 s. Different applications may utilize different connection intervals. An advantage of long connection interval is that power is saved, as the device may sleep during the time between connection events. A disadvantage of long connection intervals is that if a device has data to send, the device must wait until the next connection event. An advantage of short connection interval is that there is more opportunity for data to be sent or received, as the two devices will connect more frequently. A disadvantage is that more power will be consumed, since the device is frequently waking up for connection events. During a single connection event, one or more data packets is conveyed from one device to another device (e.g., EI to IMD or IMD to EI). For example, during a connection event, a group of four data packets may be transmitted from an EI to an IMD. During a next connection event, a group of one or more data packets may be transmitted from the IMD to the EI. Once the predefined number of data packets is transmitted during the connection event, the EI and IMD are idle until expiration of the time period corresponding to the connection interval. When a short connection interval is utilized, more data packets may be conveyed over a relatively shorter period of time. When a long connection interval is utilized, few data packets are conveyed over a relatively longer period of time.

Slave latency allows a slave device to use a reduced number of connection events. The slave latency parameter defines the number of consecutive connection events that the slave device will not need to listen for the master device. As a result, the slave device may skip a number of connection events when the slave device does not have additional data to transmit resulting in power savings. The IMD application may set the slave latency during connection establishment. When the slave latency is set to zero the slave device shall listen at every anchor point. If the slave device does not receive a data packet from the master device after applying slave latency, the slave device should listen at each anchor point and not apply slave latency until receiving a data packet from the master device.

Connection supervision timeout is a parameter that defines a maximum time between two received data packets before the connection is considered lost. A connection can break down due to various reasons such as a device moving out of range, encountering severe interference or a power failure condition. Since this may happen without any prior warning, both the master device and the slave device monitor the status of the connection. Upon reception of a valid packet, the timer is reset.

The term "connection criteria" refers to at least one of a data throughput requirement, a battery indicator or link condition of the communications link between the IMD and EI.

Various embodiments described herein include methods and systems to manage connection intervals in connection with establishing a wireless bi-directional communication link between an implantable medical device (IMD) and an external instrument (EI). The IMD may utilize leads or operate as a leadless device. During a bidirectional communications session, various types of patient related and device related data may be uploaded from the IMD to the EI. Examples of patient related data include stored electrograms (EGM), real-time EGM, patient episode related data, patient alerts and the like. Examples of device related data include device configuration information, device setting information, device status (e.g., battery status), device operational information (e.g., noise level within sensed signals, noise level within receive EI transmissions) and the like. Similarly, during the bi-directional communication session, various types of device related data may be downloaded from the EI to the IMD, such as firmware updates, device configuration updates, device setting updates and the like.

In accordance with embodiments herein, when the EI establishes the communications link with the IMD utilizing the Bluetooth Low Energy (BLE) protocol, the EI maintains multiple connection interval settings that may be switched between based on data throughput requirements, as well as other factors discussed herein. The EI initially sets a connection interval to be relative short (e.g., 20 ms) as it is anticipated that several data packet exchanges will occur during an initial segment of a communications session. For example, it may be desirable for the EI to upload device configuration and setting information from the IMD. After the initial data upload, the EI and IMD typically exchange a lower volume of data during a remaining segment of a communications session (e.g., when exchanging control commands and the like).

In accordance with embodiments herein, the EI monitors one or more connection criteria throughout the communications link. The EI compares the connection criteria to corresponding thresholds and based thereon, the EI sends special commands to the IMD to direct the IMD to change from a first connection interval to a second connection interval. For example, the EI may direct the IMD to change to a relatively long connection interval (e.g., 100 ms) based on the connection criteria. The EI may change back and forth between the long and short connection intervals (or between more than 2 connection intervals) based on current conditions of the connection criteria(s). For example, the EI may change from a long connection interval to a short connection interval when the EI determines that a large amount of data is to be transferred to/from the EI. As another example, the EI may change from a long connection interval to a short connection interval when the EI determines that a quality of the communications link has dropped below a predetermined quality of threshold.

A technical effect of at least some embodiments herein is that the connection interval may be adjusted dynamically to provide a trade-off between circumstances in which a higher data transfer rate is desired and circumstances in which a lower data transfer rate is desired. Different data transfer rates may be desirable in connection with transferring different types of data, and in connection with avoiding prolonged high current battery drain on the IMD. As one example, when it is desired to control the average battery current, even though a large amount of data is available for upload, certain types of data may be uploaded using long connection intervals, while other types of data may be uploaded using short connection intervals. For example, diagnostic data may be uploaded using longer connection intervals, while real-time EGM data may be uploaded using shorter connection intervals.

A technical effect of at least some embodiments herein is that the connection interval may be adjusted dynamically to maintain a robust communications link, such as when poor link conditions are experienced. For example, when good link conditions exist, longer connection intervals may be utilized. The connection interval may be shortened when the link condition degrades, such as due to RF noise, interference and the like. Once the noise, interference, etc. subsides, the connection interval may be lengthened again.

A technical effect of at least some embodiments herein is dynamic adjustment of the connection interval affords a benefit in connection with communications link security. It is more difficult for a third-party to "sniff" for data packets when the third-party is not aware of the connection interval. When the connection interval is repeatedly dynamically changed, this further increases the difficulty of a third-party to locate and intercept data packets.

FIG. 1 illustrates a simplified block diagram of a system 100 for initiating a bi-directional communication link. The system 100 includes an IMD 101 and an EI 201 (e.g., tablet computer, smart phone, smart watch, laptop, and/or the like), according to an embodiment. The IMD 101 may be implanted within a patient 106 (e.g., proximate to and/or within a heart 103, proximate to the spinal cord). Additionally or alternatively, the IMD 101 may have components that are external to the patient. For example, the IMD 101 may include an external pulse generator (EPG). Optionally, the IMD 101 may be one of various types of implantable devices, such as, for example, neurostimulator, an implantable pacemaker, implantable cardioverter-defibrillator (ICD), defibrillator, cardiac rhythm management (CRM) device, an implantable pulse generator (IPG), or the like.

Optionally, the IMD 101 may be a leadless pacer, examples of which are disclosed in U.S. Pat. No. 9,072,913, entitled, "RATE RESPONSIVE LEADLESS CARDIAC PACEMAKER," and U.S. Pat. No. 9,168,383, entitled "LEADLESS CARDIAC PACEMAKER WITH CONDUCTED COMMUNICATION," which are expressly incorporated herein by reference. Additionally or alternatively, the IMD 101 may be a leadless monitor, examples of which are disclosed in U.S. patent application Ser. No. 15/084,373, filed Mar. 29, 2016, entitled "METHOD AND SYSTEM TO DISCRIMINATE RHYTHM PATTERNS IN CARDIAC ACTIVITY," which is expressly incorporated herein by reference.

The EI 201 is to establish a wireless bi-directional communication link 104 with the IMD 101. The communication link 104 allows the EI 201 to receive measurements from the IMD 101, and to program or send instructions to the IMD 101. The communication link 104 may use a standard wireless protocol such as Bluetooth Low Energy, Bluetooth, Medical Implant Communication Service, and/or the like. The EI 201 may be located within a home of the patient 106, a hospital, an automobile, at an office of the patient 106, or the like.

Figure 2:
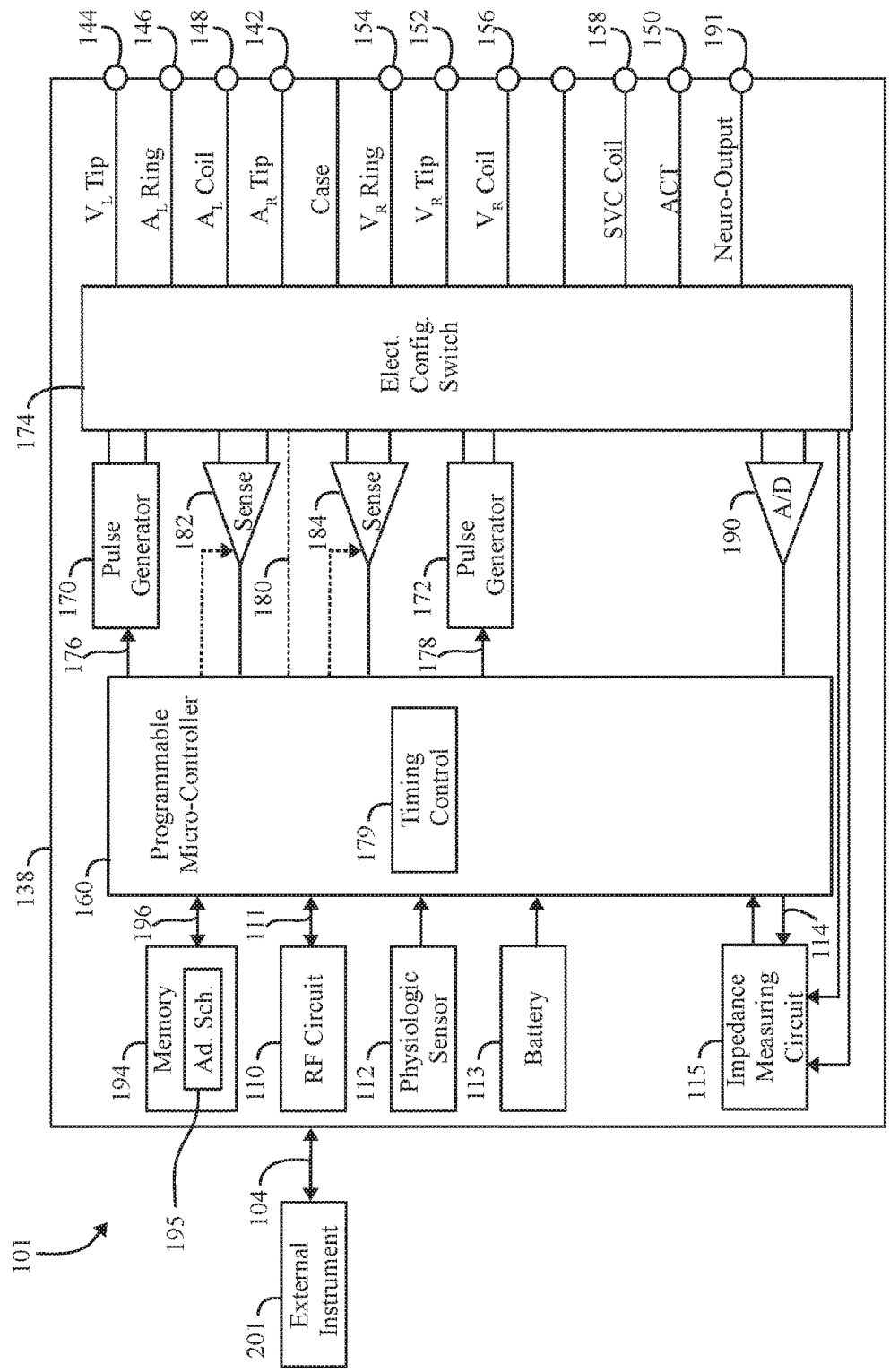
FIG. 2 illustrates a block diagram of internal components of the IMD in accordance with embodiments herein.

FIG. 2 illustrates a block diagram of internal components of the IMD 101. The IMD 101 may operate with a lead connected thereto or as a leadless IMD. The components described herein can include or represent hardware and software instructions (e.g., software stored on a tangible and non-transitory computer readable storage medium, such as a computer hard drive, ROM, RAM, or the like) that perform the operations described herein. The hardware may include electronic circuits that include and/or are connected to one or more logic-based devices, such as microprocessors, processors, controllers, or the like. Additionally or alternatively, the components may be hard-wired logic circuits.

The IMD 101 is for illustration purposes only, and it is understood that the circuitry could be duplicated, eliminated or disabled in any desired combination to provide a device capable of treating the appropriate heart chamber(s) with cardioversion, defibrillation and/or pacing stimulation as well as providing for apnea detection and therapy. Additionally or alternatively, the IMD 101 may be used to generate neurostimulation for application to a desired area of a body, such as spinal cord stimulation, the brain and the like.

The housing 138 for the IMD 101, shown schematically in FIG. 2, often referred to as the "can", "case" or "case electrode", may be programmably selected to act as the return electrode for all "unipolar" modes. The housing 138 may be a return electrode alone or in combination with one or more coil electrodes for shocking purposes. The housing 138 further includes a connector (not shown) having a plurality of terminals. The terminals may be coupled to different types of electrodes and leads. FIG. 2 illustrates various non-limiting examples of types/positions of electrodes. All or a portion of the terminals may be used in various combinations. It is recognized that alternative types of electrodes may be utilized in place of, or in addition to, the examples of FIG. 2. The following examples are provided as non-limiting examples of terminals: 142 (right atrial tip electrode), 144 (left ventricular tip electrode), 146 (left atrial ring electrode), 148 (left atrial coil electrode), 150 (acoustical terminal, ACT electrode), 152 (right ventricular tip electrode), 154 (right ventricular ring electrode), 156 (right ventricular coil electrode), and 158 (superior vena cava coil electrode). In addition, a terminal 191 is indicated to be representative of one or more neural stimulation electrodes that may be utilized in place of or in addition to the above noted electrodes.

The IMD 101 includes a controller circuit 160 which controls operation of the IMD 101. The controller circuit 160 (also referred to herein as a processor module or unit) may include one or more processors, or equivalent control circuitry, designed specifically for controlling the delivery of stimulation therapy and may further include RAM or ROM memory, logic and timing circuitry, state machine circuitry, and I/O circuitry. Typically, the controller circuit 160 includes the ability to process or monitor input signals (data) as controlled by program code stored in memory. The details of the design and operation of the controller circuit 160 are not critical to the invention. Rather, any suitable controller circuit 160 may be used that carries out the functions described herein. Among other things, the controller circuit 160 receives, processes, and manages storage of digitized cardiac data sets from the various sensors and electrodes. For example, the cardiac data sets may include IEGM data, pressure data, heart sound data, and the like.

The IMD 101 includes pulse generators 170, 172 to generate stimulation pulses for delivery by one or more leads and/or electrodes. The stimulation may be configured in different manners, such as in connection with neural stimulation, pacing pulse stimulation, cardioversion stimulation, defibrillation shocks, and the like The pulse generators, 170 and 172, may include dedicated, independent pulse generators, multiplexed pulse generators or shared pulse generators. The pulse generators, 170 and 172, are controlled by the controller circuit 160 via appropriate control signals, 176 and 178, respectively, to trigger or inhibit the stimulation pulses.

The pulse generators 170, 172 may represent atrial and/or ventricular pulse generators, where the stimulation pulses are delivered through a plurality of electrodes and/or leads located within or proximate to the heart. Optionally, the pulse generators 170, 172 may represent neurostimulation pulse generators to generate stimulation pulses for a brain or spinal cord nervous system. The stimulation pulses are delivered by a plurality of electrodes through the neuro output lead 191. The neuro stimulation pulse generator circuit is controlled by the controller circuit 160 via appropriate control signals to trigger or generate the stimulation pulses.

The controller circuit 160 further includes timing control circuitry 179 used to control the timing of such stimulation pulses (e.g., the neural stimulation waveforms, pacing rate, atria-ventricular (AV) delay, atrial interconduction (A-A) delay, or ventricular interconduction (V-V) delay, etc.) as well as to keep track of the timing of refractory periods, blanking intervals, noise detection windows, evoked response windows, alert intervals, marker channel timing, and the like. Switch 174 includes a plurality of switches for connecting the desired electrodes to the appropriate I/O circuits, thereby providing complete electrode programmability. Accordingly, the switch 174, in response to a control signal 180 from the controller circuit 160, determines the polarity of the stimulation pulses (e.g., unipolar, bipolar, etc.) by selectively closing the appropriate combination of switches (not shown).

A sensing circuit 182 and sensing circuit 184 may also be selectively coupled to one or more leads through the switch 174 for collecting sensed physiologic data (e.g., cardiac activity, neural activity, respiratory activity, etc.). The sensing circuits, 182 and 184, may include dedicated sense amplifiers, multiplexed amplifiers or shared amplifiers. The outputs of the sensing circuits, 182 and 184, are connected to the controller circuit 160 which, in turn, receives the sensed data and is able to trigger or inhibit the pulse generators, 170 and 172, respectively, in a demand fashion in response to the absence or presence of activity of interest.

Sensed signals are also applied to the inputs of an analog-to-digital (A/D) data acquisition system 190. The data acquisition system 190 is configured to acquire IEGM signals, neural signals, and the like. The data acquisition system 190 converts the raw analog data into a digital signal, and stores the digital signals in memory 194 for later processing and/or RF transmission to the EI 201. The data acquisition system 190 is coupled to one or more leads through the switch 174 to sample signals across any combination of desired electrodes. The data acquisition system 190 may also be coupled, through switch 174, to one or more of the acoustic sensors. The data acquisition system 190 acquires, performs A/D conversion, produces and saves the digital pressure data, and/or acoustic data.

An RF circuit 110 may be configured to handle and/or manage the bi-directional communication link between the IMD 101 and the EI 201. As explained herein, the RF circuit 110 transmits, among other things, advertising notices in accordance with one or more advertising schedules 195. The RF circuit 110 also scans for connection requests from the EI 201. The RF circuit 110 is controlled by the controller circuit 160 and may support one or more wireless communication protocols while communicating with the EI 201, such as Bluetooth Low Energy, Bluetooth, Medical Implant Communication Service (MICS), and/or the like. The RF circuit 110 stores parameters associated with a current CI scheme, such as a connection interval, slave latency, supervision timeout, minimum connection interval, maximum connection interval, and the like.

The RF circuit 110 may include a transmitter, receiver, and/or a transceiver. Optionally, the RF circuit 110 may be electrically coupled to an antenna (not shown). Protocol firmware may be stored in memory 194, which is accessed by the controller circuit 160. The protocol firmware provides the wireless protocol syntax for the controller circuit 160 to assemble data packets, advertisement notices, connection requests, connection responses, establish communication links 104, and/or partition data received from the EI 201.

The controller circuit 160 is coupled to the memory 194 by a suitable data/address bus 196, wherein the programmable operating parameters used by the controller circuit 160 are stored and modified, as required, in order to customize the operation of the IMD 101 to suit the needs of a particular patient. The memory 194 also stores data sets (raw data, summary data, histograms, etc.), such as the IEGM data, heart sound data, pressure data, Sv02 data and the like for a desired period of time (e.g., 1 hour, 24 hours, 1 month). The memory 194 may store instructions to direct the controller circuit 160 to analyze the cardiac signals and heart sounds, identify characteristics of interest and derive values for predetermined statistical parameters. The memory 194 stores one or more advertising schedules 195. The advertising schedule 195 may be loaded in the memory 194 at the time of manufacture, at the time of activation, at the time of installation or throughout operation. For example, an EI 201 may download one or more advertising schedules 195 to be used in connection with the corresponding EI 201. For example, when an IMD 101 initially begins communicating with a particular EI 201, the EI 201 may download a corresponding advertising schedule. Additionally or alternatively, a common advertising schedule 195 may be used with multiple EI 201. As a further example, the IMD 101 may update the advertising schedule 195 throughout operation, such as based upon the success rate at which communications links are established, based upon delays when establishing communications links and the like.

The pacing and other operating parameters of the IMD 101 may be non-invasively programmed into the memory 194 through the RF circuit 110 in bi-directional wireless communication with the EI 201. The RF circuit 110 is controlled by the controller circuit 160 and receives data for transmission over a control line 111. The RF circuit 110 allows intra-cardiac electrograms, pressure data, acoustic data, Sv02 data, and status information relating to the operation of the IMD 101 (as contained in the controller circuit 160 or memory 194) to be sent to the EI 201 through an established bi-directional communication link 104. The RF circuit 110 also allows the EI 201 to program new pacing parameters and advertising schedules for the IMD 101.

To establish the communication link 104 between the EI 201 and the IMD 101, the controller circuit 160 may instruct the RF circuit 110 to transmit one or more advertisement notices on one or more advertisement channels corresponding to an advertising schedule 195 stored in memory 194. The advertisement channel is a point to multipoint, unidirectional channel to carry a repeating pattern of system information messages such as network identification, allowable RF channels to establish the communication link 104, and/or the like, that is included within the advertisement notice. The advertisement notice may be repeatedly transmitted after a set duration or an advertisement interval based on an advertising schedule stored in the memory 194 until the communication link 104 is established with the EI 201.

The IMD 101 may also include a physiologic sensor 112, such as an accelerometer commonly referred to as a "rate-responsive" sensor because it is typically used to record the activity level of the patient or adjust pacing stimulation rate according to the exercise state of the patient. Optionally, the physiological sensor 112 may further be used to detect changes in cardiac output, changes in the physiological condition of the heart, or changes in activity (e.g., detecting sleep and wake states) and movement positions of the patient. While shown as being included within IMD 101, it is to be understood that the physiologic sensor 112 may also be external to the IMD 101, yet still be implanted within or carried by the patient. A common type of rate responsive sensor is an activity sensor incorporating an accelerometer or a piezoelectric crystal, which is mounted within the housing 138 of the IMD 101.

Other types of physiologic sensors are also known, for example, sensors that sense the oxygen content of blood, respiration rate and/or minute ventilation, pH of blood, ventricular gradient, etc. However, any sensor may be used which is capable of sensing a physiological parameter that corresponds to the exercise state of the patient and, in particular, is capable of detecting arousal from sleep or other movement.

The IMD 101 additionally includes a battery 113, which provides operating power to all of the circuits shown. Optionally, the IMD 101 may include an impedance measuring circuit 115 which is enabled by the controller circuit 160 via a control signal 114. Herein, impedance is primarily detected for use in evaluating ventricular end diastolic volume (EDV) but is also used to track respiration cycles. Other uses for an impedance measuring circuit include, but are not limited to, lead impedance surveillance during the acute and chronic phases for proper lead positioning or dislodgement; detecting operable electrodes and automatically switching to an operable pair if dislodgement occurs; measuring respiration or minute ventilation; measuring thoracic impedance for determining shock thresholds; detecting when the device has been implanted; measuring stroke volume; and detecting the opening of heart valves, etc. The impedance measuring circuit 115 is advantageously coupled to the switch 174 so that impedance at any desired electrode may be obtained.

Figure 3:
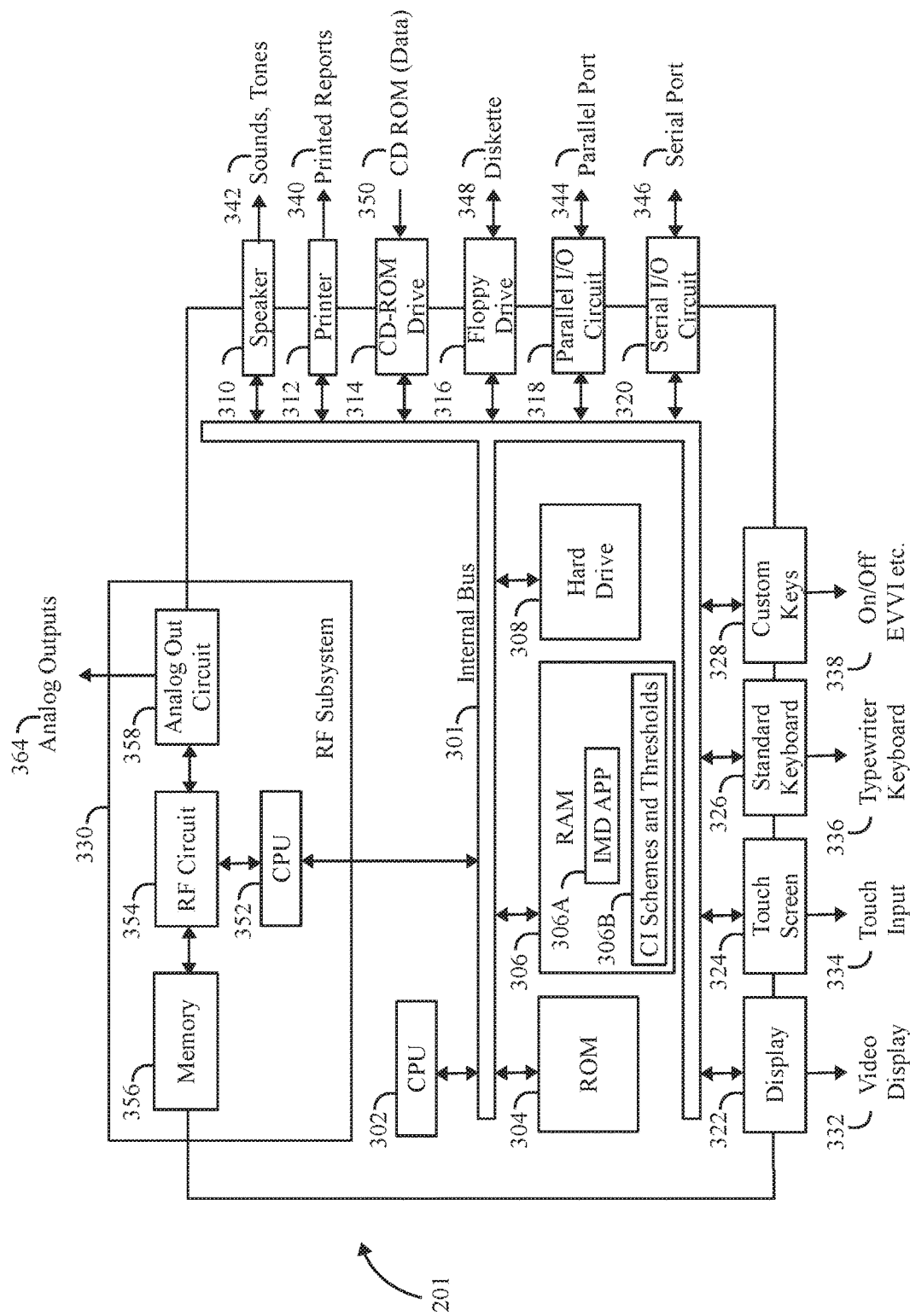
FIG. 3 illustrates a functional block diagram of the EI that is operated in accordance with embodiments herein.

FIG. 3 illustrates a functional block diagram of the EI 201 that is operated in accordance with embodiments herein. The EI 201 may be a workstation, a portable computer, a tablet computer, a smart watch, an IMD programmer, a PDA, a cell phone and/or the like. The EI 201 may include an internal bus 301 that may connect/interface with a Central Processing Unit ("CPU") 302, ROM 304, RAM 306, a hard drive 308, a speaker 310, a printer 312, a CD-ROM drive 314, a floppy drive 316, a parallel I/O circuit 318, a serial I/O circuit 320, a display 322, a touchscreen 324, a standard keyboard 326, custom keys 328, and an RF subsystem 330. The internal bus 301 is an address/data bus that transfers information between the various components described herein. The hard drive 308 may store operational programs as well as data, such as stimulation waveform templates and detection thresholds.

The CPU 302 typically includes a microprocessor, a micro-controller, or equivalent control circuitry, designed specifically to control interfacing with the EI 201 and with the IMD 101. The CPU 302 may include RAM or ROM memory, logic and timing circuitry, state machine circuitry, and I/O circuitry to interface with the IMD 101. The display 322 may be connected to the video display 332. The display 322 displays various information related to the processes described herein. The touchscreen 324 may display graphic information relating to the IMD 101 and include a graphical user interface. The graphical user interface may include graphical icons, scroll bars, buttons, and the like which may receive or detect user or touch inputs 334 for the EI 201 when selections are made by the user. Optionally the touchscreen 324 may be integrated with the display 322. The keyboard 326 (e.g., a typewriter keyboard 336) allows the user to enter data to the displayed fields, as well as interface with the RF subsystem 330. Furthermore, custom keys 328 turn on/off 338 (e.g., EVVI) the EI 201. The printer 312 prints copies of reports 340 for a physician to review or to be placed in a patient file, and the speaker 310 provides an audible warning (e.g., sounds and tones 342) to the user. The parallel I/O circuit 318 interfaces with a parallel port 344. The serial I/O circuit 320 interfaces with a serial port 346. Optionally, the serial I/O port may be coupled to a USB port or other interface capable of communicating with a USB device such as a memory stick. The floppy drive 316 accepts diskettes 348. The CD-ROM drive 314 accepts CD ROMs 350. One or more scanning schedules are stored in the RAM 306, ROM 304, on a CD ROM 350, or elsewhere.

The RF subsystem 330 includes a central processing unit (CPU) 352 in electrical communication with an RF circuit 354, which may communicate with both a memory 356 and an analog out circuit 358. The analog out circuit 358 includes communication circuits to communicate with analog outputs 364. The EI 201 may wirelessly communicate with the IMD 101 and utilize protocols, such as Bluetooth, Bluetooth Low Energy, MICS, and/or the like. For example, the memory 356, ROM 304, and/or RAM 306 may include Protocol firmware, which is accessed by the CPU 352 and/or 302. The protocol firmware provides the wireless protocol syntax for the CPU 352 and/or 302 to assemble data packets, establish communication links 104, and/or partition data received from the IMD 101. The RF subsystem 330 and CPU 352 enter scanning states and establish communication sessions as described herein.

Additionally, applications stored in the RAM 306 include an implantable medical device (IMD) application 306A that facilitates communication with the IMD, conveying program settings, updates, data, and other information for the IMD 101. The IMD application 306A also receives patient related information, device related information, and the like from the IMD 101. The IMD application 306A includes program instructions to direct the CPU 302 to complement the methods, processes, and operations described herein, and illustrated and described in connection with the FIGS.

The RAM 306 also stores multiple connection interval schemes 306B for managing the BLE link between the EI and IMD. The RAM 306 may store connection criteria (e.g., thresholds) with or separate from the CI schemes 306B. The CPU 302, under the control of the IMD application 306A, directs the RF circuit 354 to change the connection interval according to data throughput requirements, battery indicators and/or link condition (e.g., BLE signal quality) based on the dynamic connection interval scheme 306B.

Optionally, one or both of the IMD application 306A and CI schemes 306B may be stored in the ROM 304.

Advertisement and Scan Scheduling

Figure 4:
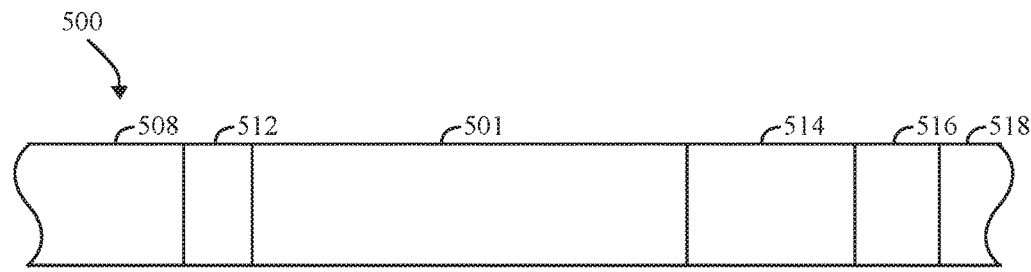
FIG. 4 is a timing diagram for establishing the BLE wireless bi-directional communication link between the IMD and the EI in accordance with embodiments herein.

FIG. 4 is a timing diagram 500 for establishing the BLE wireless bi-directional communication link 104 between the IMD 101 and the EI 201. The timing diagram 500 includes two communication sessions, a first communication session 501 and a second communication session 518. During the communication sessions 501, 518 the IMD 101 and the EI 201 may exchange data packets along the BLE wireless bi-directional communication link 104. Each of the communication sessions 501, 518 are established by the IMD 101 and the EI 201 based on advertising states 508, 514 defined as described herein. The advertising states 508, 514 are followed by an exchange of connection request and connection responses, which occurred during an interval generally referred to as establishment states 512, 516.

During the advertising states 508, 514, the IMD 101 may periodically transmit data packets corresponding to advertisement notices along one or more advertising channels. For example, the advertisement notices may be repeated at intervals defined by an advertising schedule. The advertisement notices may include frequency synchronization information utilized to form the communication link 104, address information of the IMD 101, address information of the EI 201, pairing and/or bonding information, and/or the like to form the BLE wireless bi-directional communication link 104. The information contained in the advertisement notice may be utilized by the EI 201 to establish the BLE wireless bi-directional communication link. Additionally or alternatively, the EI 201 and the IMD 101 may initiate a pairing and/or bonding procedure as described in U.S. Patent Publication No. 2015/0148868, entitled, "SYSTEM AND METHODS FOR ESTABLISHING A COMMUNICATION SESSION BETWEEN AN IMPLANTABLE MEDICAL DEVICE AND AN EXTERNAL DEVICE," which is expressly incorporated herein by reference.

During the communication session 518, the IMD 101 transmits various types of data to the EI and receives various types of data from the EI. The data throughput requirements in connection with communications sessions changes based on quantity and nature of the data. For example, the IMD 101 may upload to the EI 201 patient related data, such as EGM data or more generally patient physiologic data, acquired by the IMD 101. The IMD may upload device related data, such as configuration and setting information, battery life, transmission noise, sense noise and the like Additionally or alternatively, the EI 201 may transmit/ download reconfigure information to the IMD 101. For example, the EI 201 may transmit new stimulation parameters, clear the sensed data store in the memory 194, and/or the like. The EI 201 and/or the IMD 101 may further terminate the communication session 518 closing the BLE wireless bi-directional communication link 104 between the EI 201 and the IMD 101. When the link 104 is closed, the IMD 101 returns to a state in which the IMD 101 transmits advertisement notices in accordance with the advertising schedule.

Figure 5A:
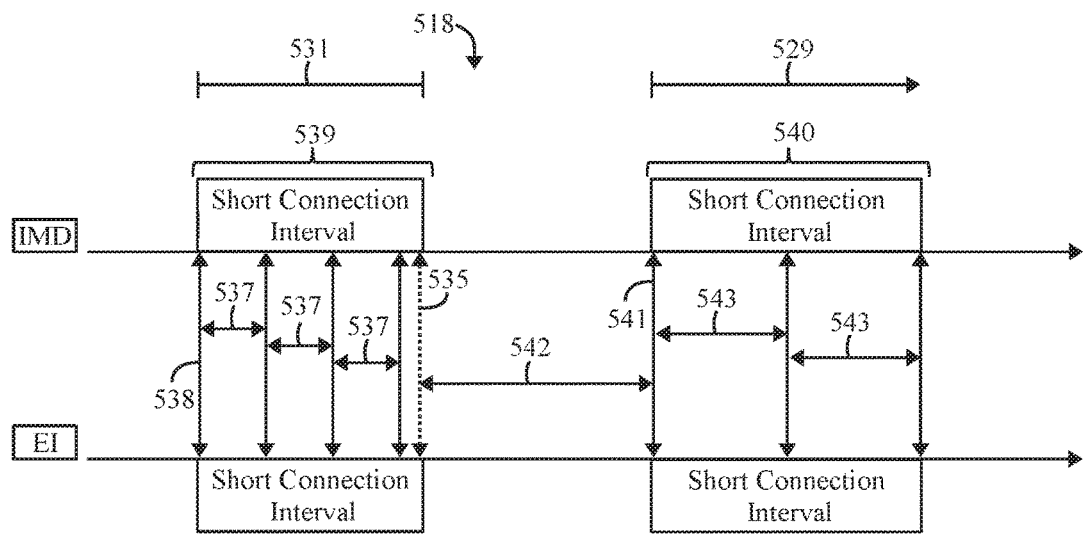
FIG. 5A illustrates a more detailed example of a communications session between an IMD and an EI in accordance with an embodiment herein.

FIG. 5A illustrates a more detailed example of the communications session 518 between an IMD and an EI in accordance with an embodiment herein. The communications session 518 follows the advertising state 514 (FIG. 4) and establishment state 516, during which the IMD and the EI establish a communications link. The communication session 518 utilizes first and second communication interval (CI) schemes 539, 540, although it is recognized that more or different CI schemes may be used.

The first and second CI schemes 539, 540 are identified by corresponding connection interval designators. A select connection interval designator is conveyed from the EI 201 to the IMD 101 to inform the IMD 101 of which CI scheme to use. The first CI scheme 539 has a first connection interval 537 which defines a time delay between transmission of successive data packets 538. At a predetermined point (e.g., the beginning) during each connection interval 537, when data is available to be transmitted, a predefined number of data packets 538 are transmitted from one of the IMD 101 and EI 201 to the other. For example, a burst of 4 data packets may be conveyed at the beginning of a series of connection intervals until all or a selection portion of the data of interest has been transmitted. Following transmission of the burst of data packets, the EI 201 and IMD 101 wait a delay until the end of the present connection interval. Upon termination of the present connection interval, the IMD 101 and/or EI 201 transmits a new burst of data packets during the next successive connection interval 537 (when data is available to be transmitted). Multiple bursts of data packets are transmitted during a corresponding number of connection intervals until all of the data of interest is transmitted, the communications session is terminated, the EI 201 determines to change the connection interval or for some other reason.

The direction in which data packets are transmitted (e.g., from the IMD to the EI or from the EI to the IMD) will vary during different communications sessions and within a communications session. For example, the IMD 101 may transmit first and second bursts of data packets during first and second connection intervals, and thereafter, the EI 201 may transmit one or more bursts of data packets during corresponding successive connection intervals.

In the example of FIG. 5A, the connection intervals 537 have the same length, although the first CI scheme 539 may be defined to include a set of connection intervals 537 that differ in length from one another in a predetermined manner.

The first CI scheme 539 represents a default scheme that may be initially used by the EI 201 and IMD 101 when the communications session 518 is initially established. The initial portion of the communications session may also be referred to as an interrogation phase 531, during which the EI 201 interrogates the IMD 101 for particular information of interest. For example, the information of interest may represent operational/critical device related data (e.g., the battery status, device operational errors, etc.). In the example of FIG. 5A, the first CI scheme 539 is used during the interrogation phase 531. As one example, the first CI scheme 539 may define the connection intervals 537 to be relatively short, relative to connection intervals in other CI schemes, such that a large number of data packets 538 may be transmitted during a relatively short period of time. When short connection intervals are utilized, less idle time exists between transmission of data packet bursts. The bi-directional communications link remains idle between the transmissions of data packets which helps to preserve IMD 101 battery life.

At various points during the communications session 518, the EI 201 determines that the CI scheme should be changed. The determination may be based on various connection criteria as discussed herein. When the EI 201 determines to change the CI scheme, the EI 201 transmits an IC designator 535 during one or more data packets 538. In the example of FIG. 5A, the IC designator 535 is transmitted during the fourth data packet 538 while utilizing the first CI scheme 539. Although the IC designator 535 may be transmitted at other times and in other manners.

In response to the IC designator 535, the IMD 101 and EI 201 enter an idle period 542, during which the EI 201 and IMD 101 switch to a new CI scheme. After the idle period 542, the communications session 518 continues with a new CI scheme. In FIG. 5A, the second CI scheme 540 is used to provide a longer connection interval 543 between transmission of data packets 541. In FIG. 5A, 3 data packets 541 are conveyed during the second CI scheme 540, and are separated by a longer connection interval 543 relative to the connection interval 537 in the first CI scheme 539. As one example, data packets 541 may be separated by a connection interval that may be twice as long as, or another multiple longer than, the connection interval 537. Optionally, the longer connection intervals 541 may be any factor larger than the shorter intervals as long as the connection interval falls within the range allowed by the corresponding communications protocol. For example, the BLE protocol allows the connection interval to range from 7.5 ms to 4 seconds. The EI 201 continues to utilize the longer connection interval scheme for a desired amount of time. For example, the second CI scheme 540 may be utilized throughout a standard interaction phase 529 of the communications session 518, until the EI 201 determines that a connection criteria has crossed a threshold, such as to indicate a need for a higher data transfer rate (also referred to as a higher frequency).

Figure 5B:
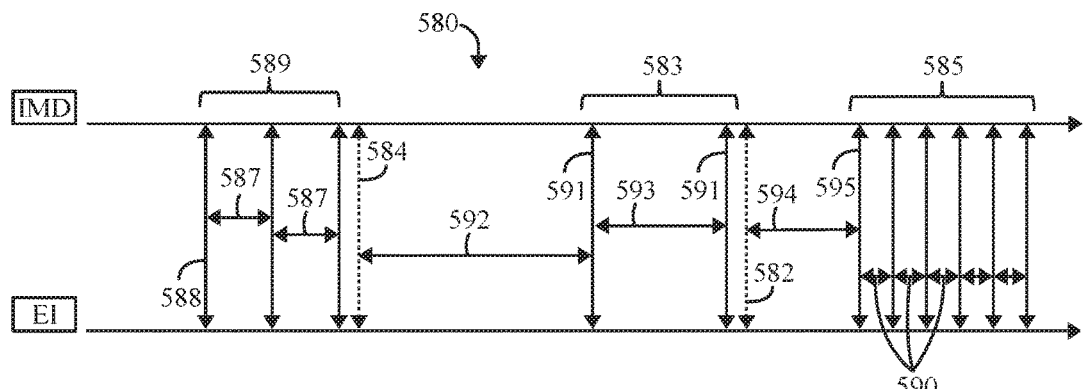
FIG. 5B illustrates an example of an advertising schedule, a scanning schedule, and communications session that uses dynamic connection intervals in accordance with an embodiment herein.

FIG. 5B illustrates an example of a communications session that uses dynamic connection intervals in accordance with an embodiment herein. Prior to establishing a communications session 580, the IMD 101 and EI 201 performed transmitting and scanning operations independently of one another. The IMD 101 and EI 201 perform advertising and scanning operations asynchronously, with respect to one another. The IMD 101 enters the advertising state, remains in the advertising state, and terminates the advertising state in accordance with a predetermined protocol independent of, and without knowledge of, the scanning schedule or scanning state of the EI 201.

Similarly, prior to establishing the communications session 580, the EI 201 enters, remains in, and terminates the scanning state in accordance with the scanning schedule independent, and without knowledge, of the advertising schedule or advertising state of the IMD 101. The EI 201 remains in the scanning state until the IMD 101 and EI 201 begin exchanging connection information. When the IMD 101 and EI 201 exchange connection information, the IMD 101 and EI 201 may be considered in the establishing state 512 (FIG. 4) to establish a communications session therebetween.

During the advertising state, the IMD 101 transmits advertisement notices based on a predetermined advertising schedule. The advertising schedule defines a pattern for the advertisement notices, in which the advertisement notices are distributed unevenly, and separated by unequal advertisement intervals. Each advertisement notice has a predetermined notice duration, during which the IMD 101 conveys advertisement information. The advertisement information represents one or more data packets that may contain various information, such as frequency synchronization information utilized to form the BLE bi-directional communication link 104 (FIG. 1), address information of the IMD 101, address information of the EI 201, and/or the like. The advertising information may contain additional data and information as defined by the BLE wireless protocol. Additionally or alternatively, the advertisement notices may include pairing and/or bondable information (e.g., passkey seed information). The advertisement notices repeat based on the adverting schedule until the BLE wireless bi-directional communication link 104 is established. Turning to the EI 201, the EI 201 scans for advertisement notices during a scanning window based on a scanning schedule. The scanning schedule defines a pattern for the scanning windows, which has a predetermined scan duration between the scanning windows that may be equal to one another. The IMD 101 and EI 201 operate asynchronously with respect to one another.

During the scanning window, the EI 201 detects the advertisement notice. In response thereto, the EI 201 transmits a connection request to the IMD 101. The IMD 101 receives the connection request and in response thereto, returns a connection response immediately thereafter. When the EI 201 detects the advertisement notice, the IMD 101 and EI 201 enter the establishing state 512 (FIG. 4). The EI 201 returns the connection request, followed by the IMD 101 transmitting a connection response. Thereafter, the communication session is established. In accordance with one embodiment, the EI 201 transmits an IC designator to the IMD 101 during the establishing state.

In FIG. 5B, first, second and third CI schemes 589, 583 and 585 are illustrated. The CI schemes 589, 583, 585 have corresponding different connection intervals 587, 593 and 590. The first CI scheme 589 utilizes the connection interval 587 that is intermediate in length between the length of the connection intervals 593 and 590 used with the second and third CI schemes 583 and 585.

An intermediate length may be used as the default connection interval 587 when the connection event (e.g., an interrogation phase) calls for bursts of data packets 588 at an intermediate data transfer rate. The EI 201 determines dynamically to change to a different data transfer rate (e.g., faster or slower) based on various factors. In FIG. 5B, the EI 201 conveys an IC designator 584 to direct the IMD 101 to switch to the second CI scheme 583, helping to preserve IMD 101 battery life. After an idle period 592, the communications session 580 continues with a longer CI scheme 583 for the transmitted data packets 591. Data packets 591 are separated by a longer connection interval 593 relative to the connection intervals 587 and 590. The EI 201 continues to keep the IMD 101 in the second CI scheme 583 until a factor indicates a desire to change. An IC designator 582 is transmitted to the IMD 101, followed by an idle period 594 before continuing the communications session 580 with a third CI scheme 585 that utilizes a shorter connection interval 590 between data packets 595.

Figure 6A:
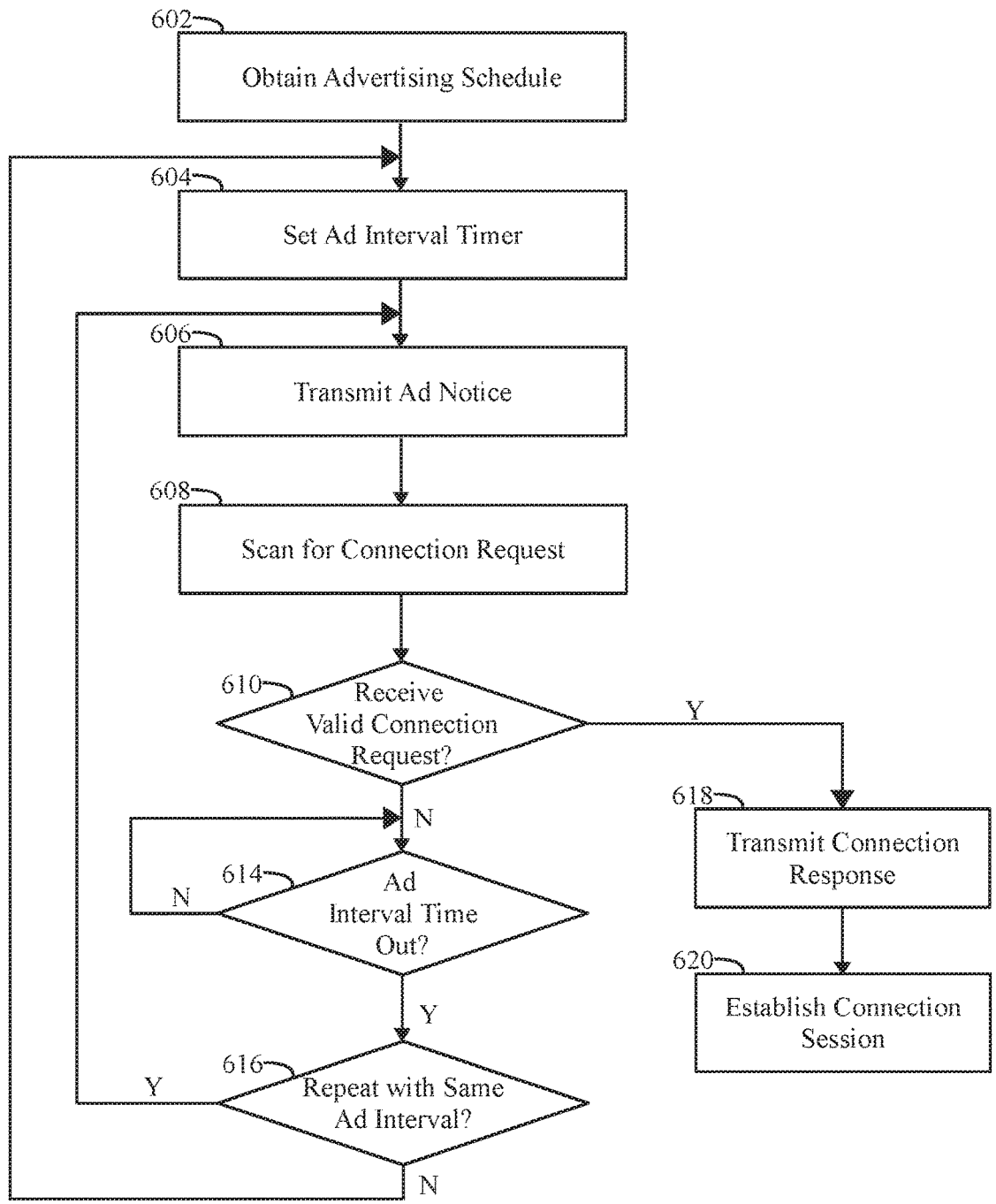
FIG. 6A illustrates a flowchart of a method for managing advertising and scanning schedules utilized for establishing of a bi-directional BLE communication link between the EI and the IMD in accordance with embodiments herein.
Figure 6B:
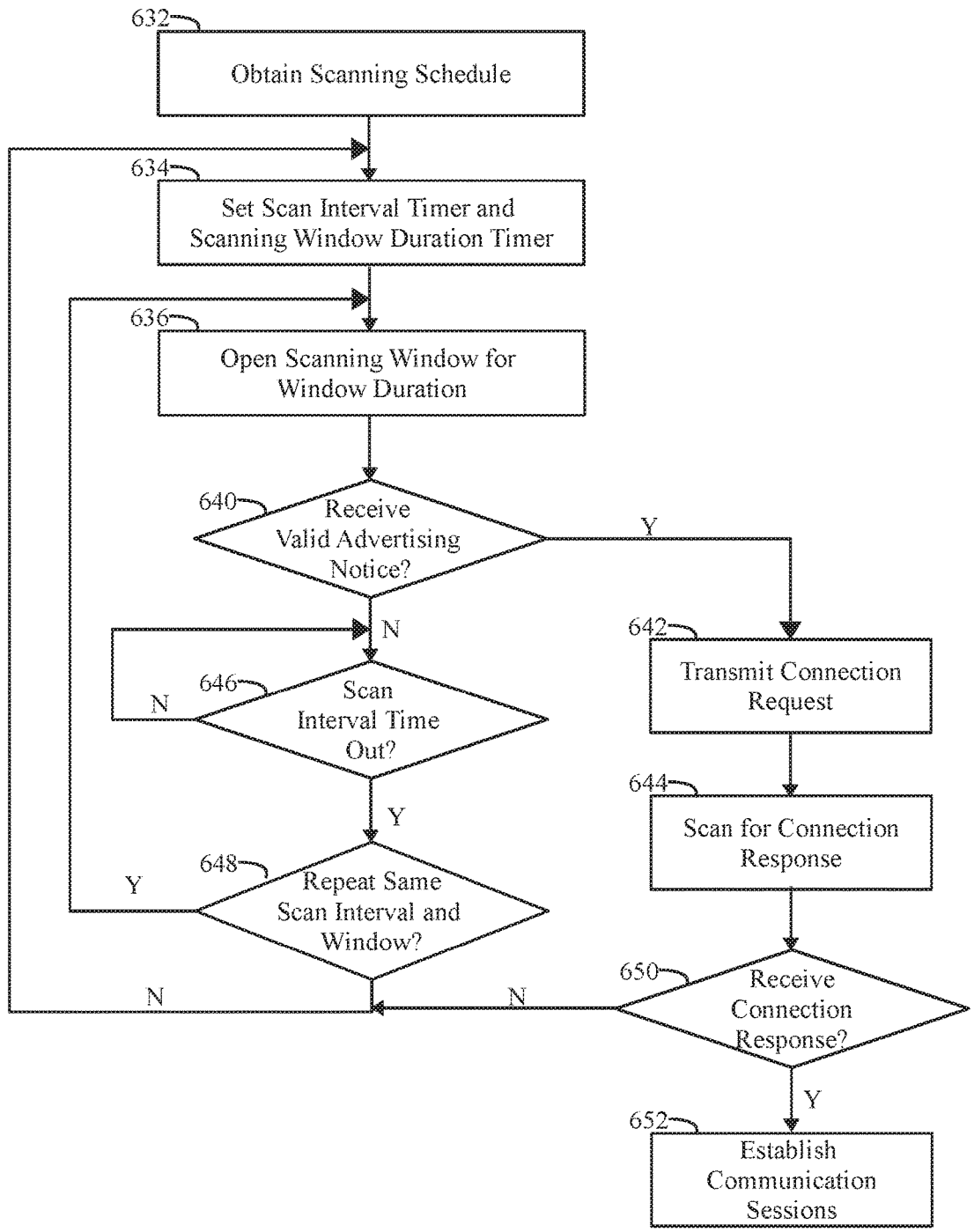
FIG. 6B illustrates a flowchart of a method for managing advertising and scanning schedules utilized for establishing of a bi-directional BLE communication link between the EI and the IMD in accordance with embodiments herein.

FIGS. 6A and 6B illustrate flowcharts of a method for managing advertising and scanning schedules utilized for establishing of a bi-directional BLE communication link between the EI 201 and the IMD 101. The method may be implemented as a software algorithm, package, or system that directs one or more hardware circuits or circuitry to perform the actions described herein. For example, the operations of the method may represent actions to be performed by one or more circuits that include or are connected with processors, microprocessors, controllers, microcontrollers, Application Specific Integrated Circuits (ASICs), Field-Programmable Gate Arrays (FPGAs), or other logic-based devices that operate using instructions stored on a tangible and non-transitory computer readable medium (e.g., a computer hard drive, ROM, RAM, EEPROM, flash drive, or the like), such as software, and/or that operate based on instructions that are hardwired into the logic of the.

FIG. 6A illustrates a flowchart for a method performed by the IMD 101 during the advertising state. At 602, the processor of the IMD 101 obtains an advertising schedule stored in memory. At 604, the processor sets an advertising interval timer to an advertising interval based on the advertising schedule. At 606, the transmitter of the IMD 101 (e.g., RF circuit 110) transmits an advertisement notice. At 608, a receiver within the IMD 101 (e.g., RF circuit 110) scans one or more channels for a connection request. At 610, the processor of the IMD determines whether an incoming connection request is valid. For example, when a connection request is received, the content of the connection request is analyzed by the processor to determine whether the connection request is directed to the IMD 101 and has been transmitted from an authorized EI 201. For example, connection requests may be transmitted by various wireless devices. The IMD 101 may receive such connection requests even though various connection requests are not directed to the IMD 101, nor transmitted from an authorized EI 201. As one example, a valid connection request may include identification information corresponding to the IMD 101. For example, when the IMD 101 conveys an advertisement notice, the advertisement notice may include a serial number or other identification information unique to the IMD 101. An authorized EI 201, upon receiving an advertisement notice, returns the serial number and/or other identification information in a connection request. At 610, the IMD 101 analyzes the content of incoming connection request for the serial number and/or other identification information originally transmitted from the IMD 101 in advertisement notice.

At 610, when a valid connection request is received, flow branches to 618. At 618, the advertising state is terminated and an establishing state is initiated in connection with establishing a communication session. At 618, the transmitter of the IMD 101 transmits a connection response. At 620, the IMD 101 and the EI 201 establish a communications session.

Alternatively, at 610, when no connection request is received or an invalid connection request is received, flow continues to 614. At 614, the processor of the IMD waits for the advertising interval timer to time out. At 614, when the interval timer times out, flow continues to 616. At 616, the processor of the IMD determines whether to repeat another advertising operation using the same advertising interval. When the same advertising interval is repeated for the next advertisement notice, flow returns to 606. Otherwise, flow returns to 604 where a new advertising interval is set from the advertising schedule.

FIG. 6B illustrates a flowchart for a method performed by the EI 201 during the scanning state. At 632, the processor of the EI 201 obtains a scanning schedule stored in memory. At 634, the processor sets a scanning interval timer to a scanning interval based on the scanning schedule. At 636, the receiver of the EI 201 opens a scanning window to scan for an advertisement notice. The receiver scans one or more channels for an advertisement notice. At 640, the processor of the EI 201 determines whether an advertisement notice was detected and if so, whether the incoming advertisement notice is from the IMD 101. For example, when an advertisement notice is received, the content of the advertisement notice is analyzed by the processor to determine whether the advertisement notice is directed to the EI 201 and has been transmitted from an authorized IMD 101. Advertisement notices are transmitted by various wireless devices. The EI 201 may detect advertisement notices from various devices, even though the advertisement notices are not directed to the EI 201, nor transmitted from the IMD 101. As one example, a valid advertisement notice may include identification information corresponding to the IMD 101. For example, when the IMD 101 conveys an advertisement notice, the advertisement notice may include a serial number or other identification information unique to the IMD 101. When a valid advertisement notice is detected, flow branches to 642. Otherwise flow continues to 646.

At 642, upon receiving a valid advertisement notice, the EI 201 returns a connection request. For example, the connection request may include an EI serial number and/or other EI identification information. The connection request may also include information from the advertisement notice. At 644, the EI 201 scans for a connection response. As explained above in connection with FIG. 6A, when the IMD 101 detects a valid connection request, the IMD 101 returns a connection response.

At 650, the processor determines whether a connection response was received. When a connection response is received, flow moves to 652 where a communication session is established. Alternatively, when no connection response is received, at 650 flow branches to continue the scanning operations. In the example of FIG. 6B, when no connection response is received, the process may return to 634 where a new scanning interval timer and scanning window duration timer are set. Alternatively, flow may return to various other points within the operations of FIG. 6B. At 652, the scanning state terminates and the establishing state initiates in connection with establishing a communication session.

Alternatively, at 640, when no advertisement notice is received or an invalid advertisement notice is received, flow continues to 646. At 646, the processor of the EI 201 waits for the scanning interval timer to time out. At 646, when the interval timer times out, flow continues to 648. At 648, the processor of the EI 201 determines whether to repeat another scanning operation using the same scanning interval. When the same scanning interval is to be repeated for the next scanning window, flow returns to 636. Otherwise, flow returns to 634 where a new scanning interval is set.

Figure 7A:
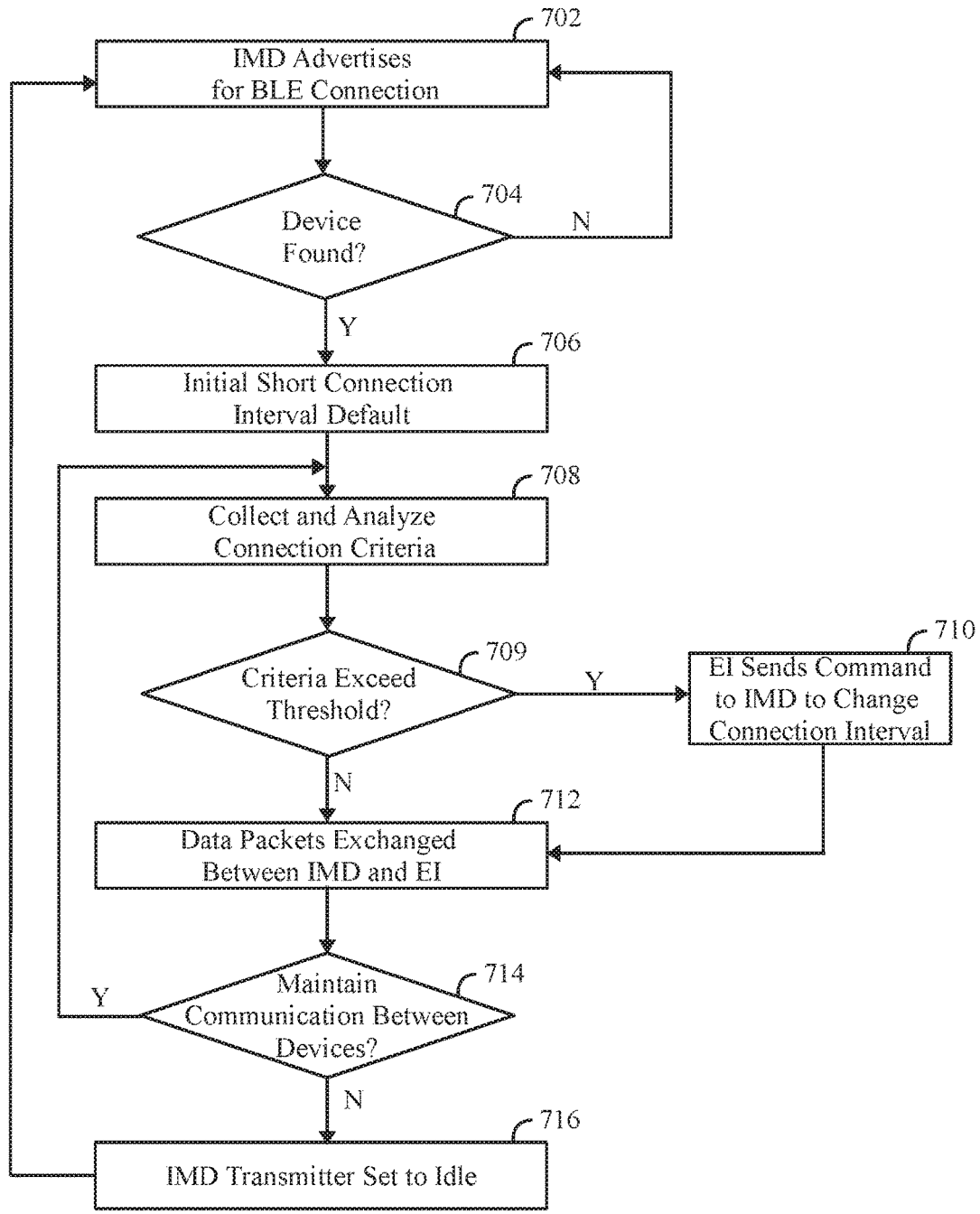
FIG. 7A illustrates a process for dynamically changing between CI schemes during a communications session in accordance with embodiments herein.

FIG. 7A illustrates a process for dynamically changing between CI schemes during a communications session in accordance with embodiments herein. The method may be implemented as a software algorithm, package, or system that directs one or more hardware circuits or circuitry to perform the actions described herein. For example, the operations of the method may represent actions to be performed by one or more circuits that include or are connected with processors, microprocessors, controllers, microcontrollers, Application Specific Integrated Circuits (ASICs), Field-Programmable Gate Arrays (FPGAs), or other logic-based devices that operate using instructions stored on a tangible and non-transitory computer readable medium (e.g., a computer hard drive, ROM, RAM, EEPROM, flash drive, or the like), such as software, and/or that operate based on instructions that are hardwired into the logic of the.

At 702, the processor of the IMD 101 enters an advertising state for a BLE connection from an EI 201. At 704, the processor of the IMD 101 determines whether the IMD 101 has connected to an EI 201. As explained herein, the transmitter of the IMD 101 repeats the transmitting operation over one or more advertising states, until detecting a connection request from the EI 201. At 706, upon successfully establishing a BLE link, the initial dynamic connection interval defaults to a short interval.

At 708, the processor of the EI 201 collects and analyzes the connection criteria that vary based on the connection interval. The connection criteria includes at least one of a data throughput requirement, a battery indicator or link condition of the communications link between the IMD and EI. At 709, the processor of the EI 201 determines whether one or more of the connection criteria exceeds one or more thresholds.

The data throughput requirement represents a connection criteria associated with an amount and/or type of data that is available to be transferred between the EI 201 and IMD 101. Examples of data types are device related data and patient related data. Examples of device related data are configuration or settings data stored on the IMD 101, firmware updates stored at the EI 201, updates to IMD settings stored at the EI 201 and the like. Examples of patient related data are real-time physiologic measurements (e.g., EGM data, breathing rate data, neurological data). The data may reside on the IMD 101 and/or on the EI 201. For example, the IMD 101 may have configuration data to download to the EI 201 at a beginning of a communications session. Optionally, the EI 201 may have new setting data (e.g., defining new program settings from a physician) to be uploaded to the IMD 101 from the EI 201. As another example, the IMD 101 may have stored EGM data, episode data and the like for a period of time to be uploaded to the EI 201. The IMD 101 may include a large amount of patient related data to be transferred to the EI 201, such as stored EGM and episode data for an extended period of time. The IMD 101 may also sense real-time physiologic data (EGM data) that is downloaded to the EI 201 as soon as recorded. The EI 201 may have large or small amounts of data to upload to the IMD 101. For example, firmware updates may involve a large amount of data to be transferred to/from the IMD 101, while physician updates to IMD operational settings may involve a small amount of data. When the IMD 101 and/or the EI 201 includes a large amount of data to be transferred, it is preferred that the IMD 101 and the EI 201 utilize a high data throughput.

At 708 and 709, the processor of the EI 201 also evaluates a battery indicator indicative of a condition of the IMD battery. The battery indicator may characterize the battery in different manners. For example, the battery indicator may indicate an amount of charge remaining in the battery, an average current drain over a predetermined period of time, a battery age, discharge curves associated with the battery and the like. The battery indicator may also represent an estimate of a remaining battery life, such as based on recent activity by the IMD 101. For example, a first IMD 101, that delivers therapy frequently, may have a same charge as a battery in a second IMD 101 that delivers therapy less frequently. Based on the foregoing example, the battery indicator for the first IMD may estimate a shorter remaining life than a remaining life of the battery in the second IMD.

At 708 and 709, the processor of the EI 201 also evaluates a link condition of the communications link between the EI 201 and IMD 101. For example, the link condition may indicate whether the quality of the communications link is sufficient for various data transfer rates. Examples of link conditions are signal to noise ratio (SNR), error bit rate, and the like. When the link condition is poor (e.g., low SNR, high error bit rate, etc.), it may be preferred to utilize a shorter connection interval as compared to good link conditions. For example, when the link conditions are poor, transmission errors may occur, such as errors in received data packets. When detecting a data packet error, the data packet is retransmitted in a subsequent connection interval. By shortening the connection interval when poor link conditions exist, the transmission scheme allows more data packets to be retransmitted in a shorter period of time. Accordingly, data transmission errors are overcome sooner as erroneous data packets can be retransmitted sooner (when using a short connection interval) as compared to utilizing a long connection interval.

At 709, the processor of the EI 201 determines whether one or more of the connection criteria satisfy or exceed corresponding thresholds. At 709, flow branches to 710 or 712 based on whether the connection criteria satisfy or exceed the corresponding thresholds. Flow branches to 710 when the processor determines to change the CI scheme to change the connection interval. At 710, the processor of the EI 201 transmits an interval command to the IMD 101 directing the IMD 101 to change to a different connection interval. For example, when the present connection interval corresponds to a first/short connection interval, at 710, the processor may transmit an interval command to switch to a second CI scheme having a second/long connection interval. Alternatively, when the present connection interval corresponds to the second/long connection interval, at 710, the processor may transmit an interval command to switch to the first CI scheme having the first/short connection interval. Optionally, the interval command may designate a third or fourth CI scheme.

At 712, the IMD 101 and EI 201 exchange data packets utilizing the CI scheme designated by the processor of the EI 201. At 714, the processor of the EI 201 determines whether to maintain the communications link between the IMD and EI or to disconnect. When the present communications session is to be maintained, flow returns to 708 where the connection criteria are collected and analyzed again. Otherwise, flow continues to 716. At 716, the processor of the EI 201 (and/or of the IMD 101) directs the IMD 101 to disconnect and terminate the present communications session. The transmitter of the IMD 101 is set to idle to conserve IMD battery life, while waiting for the next communications session.

It should be recognized that the EI 201 may be used with various IMD, and vice versa. Accordingly, different CI schemes may be utilized with different combinations of EI and IMD. Optionally, the method of FIG. 7A may be repeated to change the CI scheme in one or more manners. For example, the CI scheme may be changed by changing slave latency, supervision timeout, minimum connection interval, maximum connection interval, and the like. For example, the CI scheme may be changed when the EI 201 detects an unduly large number of connection events. Additionally or alternatively, the processor of the EI 201 may change the CI scheme based upon different IMD that are communicating there with. For example, the EI 201 may be configured to communicate with multiple IMDs. Each IMD may have a different data throughput requirements, link conditions, power requirements and the like. The processor of the EI 201 may determine that the EI 201 is to communicate with a new IMD. In connection there with, the processor of the EI 201 may change from a first IC scheme associated with a first IMD, to a second CI scheme associated with a second IMD. It should be recognized that various CI schemes may be useful with various different IMDs, however, different CI schemes may be tailored to correspond to the individual IMD.

Figure 7B:
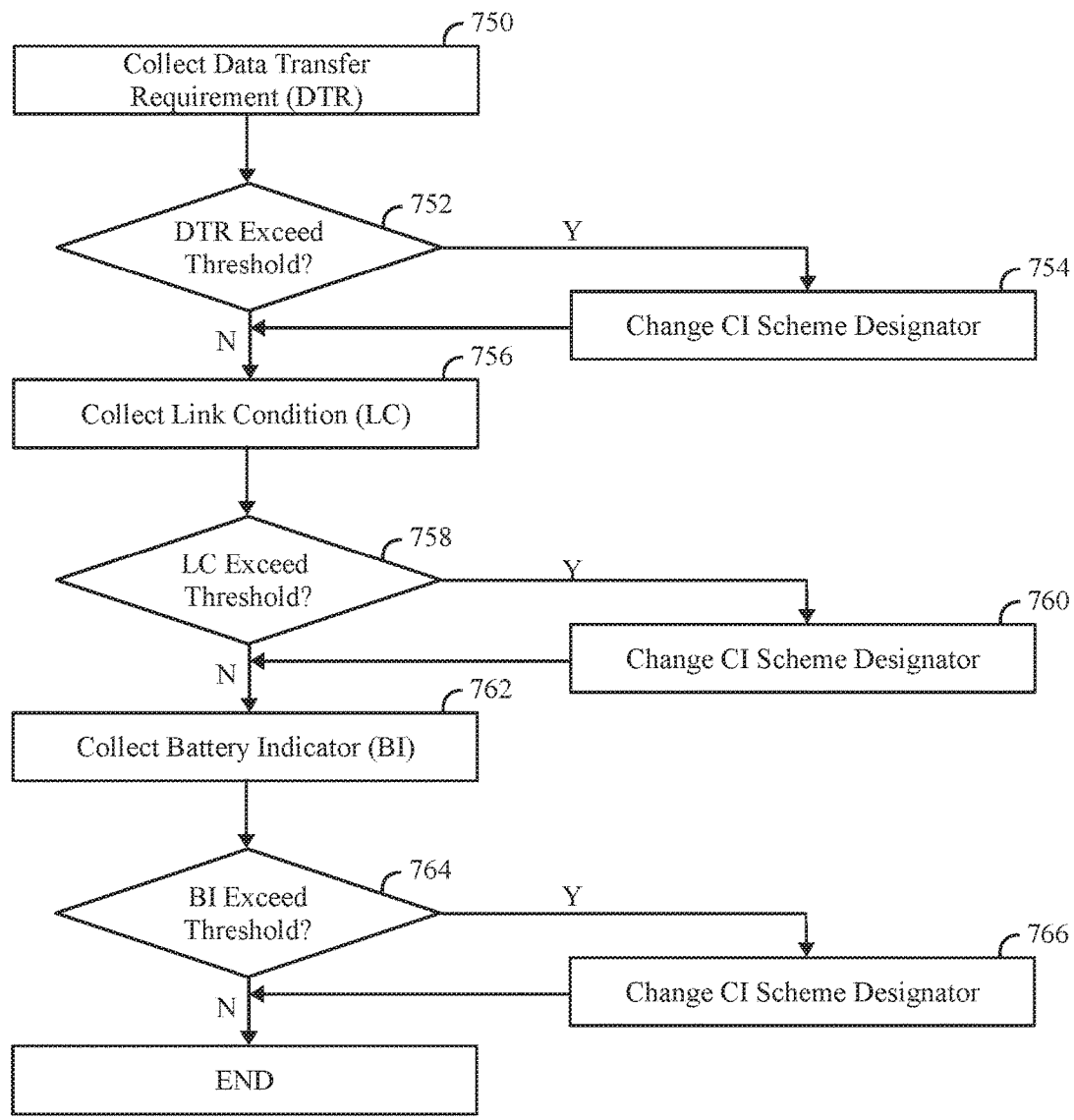
FIG. 7B illustrates a process for analyzing connection criteria during a communications session in accordance with embodiments herein.

FIG. 7B illustrates a process for analyzing connection criteria during a communications session in accordance with embodiments herein. By way of example, the operations of FIG. 7B may be implemented during 708 in FIG. 7A. The method may be implemented as a software algorithm, package, or system that directs one or more hardware circuits or circuitry to perform the actions described herein. For example, the operations of the method may represent actions to be performed by one or more circuits that include or are connected with processors, microprocessors, controllers, microcontrollers, Application Specific Integrated Circuits (ASICs), Field-Programmable Gate Arrays (FPGAs), or other logic-based devices that operate using instructions stored on a tangible and non-transitory computer readable medium (e.g., a computer hard drive, ROM, RAM, EEPROM, flash drive, or the like), such as software, and/or that operate based on instructions that are hardwired into the logic.

As explained herein, the connection criteria may include one or more of a data transfer requirement, a battery indicator or link condition of the communications link between the IMD and EI. The process of FIG. 7B analyzes the foregoing types of connection criteria, although one or more of the connection criteria may be omitted and/or another connection criteria may be analyzed.

At 750, the processor of the EI 201 collects a current data transfer requirement (DTR) of the IMD 101 and/or the EI 201. The current data transfer requirement may represent an amount/quantity of data stored and ready for transfer. Additionally or alternatively, the current data transfer requirement may designate the type of data to be transferred. As one example, the data transfer requirement may represent a number indicative of the amount/quantity of data and/or a descriptor characterizing the type of data. Additionally or alternatively, the data transfer requirement may represent a rating, such as a high data rate, low data rate, medium data rate. As another example, the data transfer requirement may represent a rating on a scale (e.g., between one and 10).

At 752, the processor of the EI 201 compares the current data transfer requirement to one or more thresholds. For example, the threshold may represent an amount or quantity of data that represent transition points between high, low or medium data rates. When the DTR falls within the thresholds, flow moves to 756. When the DTR exceeds (or otherwise falls outside of) the threshold(s), flow moves to 754. At 754, the processor changes the CI scheme designator. The change in the CI scheme designator at 754 would depend upon the current CI scheme and the manner in which the DTR exceeds the threshold. For example, when the present CI scheme corresponds to a high data transfer rate, yet the DTR, relative to the threshold, indicates that a low data transfer rate is appropriate, at 754, the CI scheme may be changed to a CI scheme corresponding to a lower data transfer rate. Alternatively, when the present CI scheme corresponds to a low data transfer rate, and the DTR (relative to the threshold) indicates a desire for a high data transfer rate, at 754, the CI scheme may be changed to a CI scheme corresponding to a high data transfer rate.

At 756, the processor of the EI 201 collects a link condition (LC). The link condition may be based on a quality of communications received at the IMD 101, such as an indication of the signal-to-noise ratio, bit error rate, etc., experienced by incoming data transmissions to the IMD 101. Additionally or alternatively, the link condition may correspond to a quality of incoming communications to the EI 201. Additionally or alternatively, the link condition may be based on a combination of quality indicators collected by the IMD 101 and EI 201. At 758, the processor compares the link condition information to one or more thresholds. When the link condition falls within the thresholds, flow moves to 762. When the link condition exceeds (or otherwise falls outside of) the corresponding threshold(s), flow transfers to 760. At 760, the processor changes the current CI scheme designator. In accordance with an embodiment, the current CI scheme designator at 760 corresponds to the CI scheme designator resulting from the analysis at 750-754. In the present example, the change at 760 may be cumulative with a change (or no change) at 754.

At 762, the processor of the EI collects a battery indicator (BI). As explained herein, the battery indicator may be representative of various characteristics of the battery in the IMD 101. At 764, the battery indicator is compared to one or more thresholds. When the battery indicator falls within the corresponding thresholds, the process ends. When the battery indicator exceeds (or otherwise falls outside of) the corresponding threshold(s), flow moves to 766. At 766, the processor changes the current CI scheme designator. In accordance with an embodiment herein, the current CI scheme designator at 766 may correspond to the result of the changes at 754 and 760.

In accordance with the embodiment of FIG. 7B, the changes at 754, 760 and 766 may build upon one another. Optionally, the changes at 754, 760, 766 may be performed separately and in parallel. For example, the changes in the CI scheme designator based on the different connection criteria may be merged based on various weighting factors. For example, changes to the CI scheme based on the battery indicator may be afforded a greatest weight, while changes based on data transfer requirements and link conditions may be afforded a lesser weight.

Figure 8:
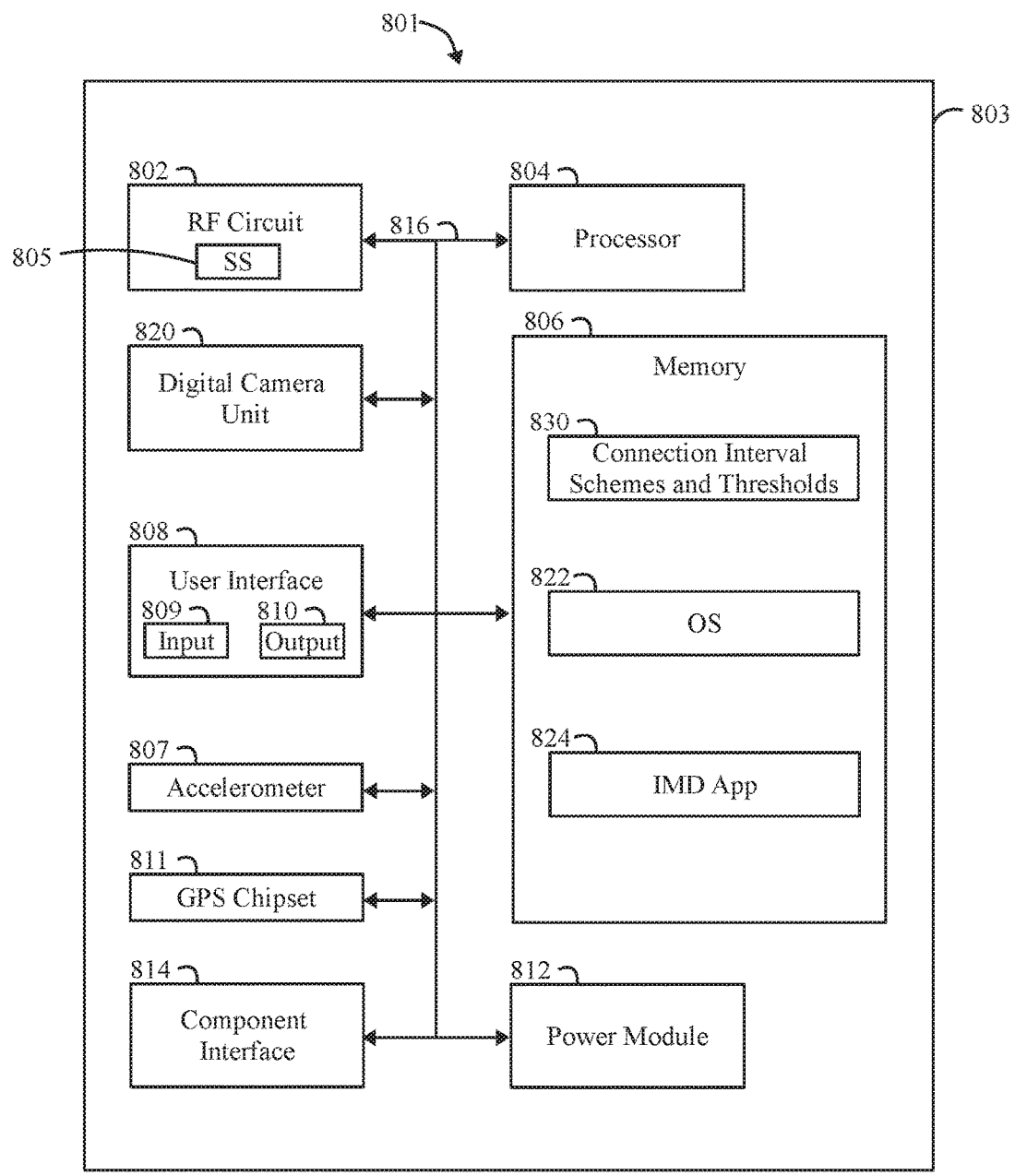
FIG. 8 illustrates a simplified block diagram of an external instrument (EI) formed in accordance with embodiments herein.

FIG. 8 illustrates a simplified block diagram of an external instrument (EI) 801 formed in accordance with embodiments herein. The EI 801 includes one or more wireless RF circuits 802, and one or more processors 804 (e.g., a microphone, microcomputer, application-specific integrated circuit, etc.). The EI 801 also includes one or more local storage medium (also referred to as a memory) 806, a GPS chipset 811, an accelerometer 807, a power module 812, a digital camera unit 820, and a component interface 814. The EI 801 also includes a user interface 808 that includes one or more input devices 809 and one or more output devices 810. The components of the EI 801 are operatively coupled to one another, and may be in communication with one another, by way of one or more internal communication links 816, such as an internal bus.

A housing 803 holds the processor(s) 804, memory 806, user interface 808, the digital camera unit 820 and other components. The input and output devices 809, 810 may each include a variety of visual, audio, and/or mechanical devices. For example, the input devices 809 can include a visual input device such as an optical sensor or camera, an audio input device such as a microphone, and a mechanical input device such as a keyboard, key pad, selection hard and/or soft buttons, switch, touchpad, touch screen, icons on a touch screen, a touch sensitive, area on a touch sensitive screen and/or ant combination thereof. Among other things the microphone may be utilized to record spoken requests from the user. Similarly, the output devices 810 can include a visual output device such as a liquid crystal display screen, one or more light emitting diode indicators, an audio output device such as a speaker, alarm and/or buzzer, and a mechanical output device, such as a vibrating mechanism. Among other things, the speaker may be used to state instructions, ask questions and otherwise interact with the user. The display may be touch sensitive to various types of touch and gestures. As further examples, the output device(s) 810 may include a touch sensitive screen, a non-touch sensitive screen, a text-only display, an audio output (e.g., a speaker or headphone jack), and/or any combination thereof. The user interface 808 permits the user to select one or more of a switch, button or icon in connection with normal operation of the EI 801.

The power module 812 preferably includes a power supply, such as a battery, for providing power to the other components while enabling the EI 801 to be portable, as well as circuitry providing for the battery to be recharged. The component interface 814 provides a direct connection to other devices, auxiliary components, or accessories for additional or enhanced functionality, and in particular, can include a USB port for linking to a user device with a USB cable. The GPS chipset 811 obtains GPS location information concerning the present position of the device. The accelerometer 807 detects movement and orientation of the EI 801.

The RF circuit 802 will utilize BLE wireless technology for communication. The RF circuit 802 may represent one or more transmitters, one or more receivers and/or one or more transceivers that execute firmware in accordance with a corresponding communications protocol. The RF circuit 802 may include one or more local processors as part of, or in addition to, the transmitters, receivers, or transceivers. The RF circuit 802 executes firmware that includes, among other things, a scan schedule 805 that defines the durations of the scanning windows, scanning intervals, distribution of the scanning windows throughout a scanning state, duty cycle and the like.

The RF circuit 802 is controlled by the processor 804. Optionally, the RF circuit 802 may be electrically coupled to an antenna (not shown). Optionally, protocol firmware may be stored in memory 806, which is accessed by the processor 804. The protocol firmware provides the wireless protocol syntax for the processor 804 to assemble data packets, advertisement notices, connection requests, connection responses, establish communication links, and/or partition data received from the IMD.

The memory (local storage medium) 806 may encompass one or more memory devices of any of a variety of forms (e.g., read only memory, random access memory, static random access memory, dynamic random access memory, etc.) and can be used by the processor 804 to store and retrieve data. The data that is stored by the memory 806 can include, but need not be limited to, operating systems, applications, and informational data. The data that is stored by the memory 806 can include applications and informational data. The operating system includes executable code that controls basic functions of the communication device, such as interaction among the various components, communication with external devices via the wireless RF and/or the component interface 814, and storage and retrieval of applications and data to and from the memory 806. Each application includes executable code that utilizes an operating system to provide more specific functionality for the communication devices, such as filesystem service and handling of protected and unprotected data stored in the memory 806.

Applications stored in the memory 806 include various application programming interfaces (APIs). Additionally, the applications stored in the memory 806 include an implantable medical device (IMD) application 824 that facilitates communication with the IMD, conveying program settings, updates, data, and other information for the IMD. The IMD application 824 also receives patient related information, device related information, and the like from the IMD. The IMD application 824 includes program instructions to direct the processor 804 to complement the methods, processes, and operations described herein, and illustrated and described in connection with the FIGS.

In accordance with at least some embodiments, the RF circuit 802 stores (in local memory) the scanning schedule 805. The RF circuit 802 is configured to enter the scanning state in response to a start scan request from the processor 804. The RF circuit 802 maintains the scanning state, during which scanning windows are opened and closed by the RF circuit 802 in accordance with the scanning schedule 805. As explained herein, the distribution of the scanning windows may vary according to different scanning schedules. For example, the scanning windows may be unevenly distributed across the base scanning schedule with at least a portion of the scanning windows grouped in a first segment of the scanning state. As one example, the base scanning schedule 805 may represent a Bluetooth connection schedule that is stored with in the firmware on the RF circuit 802 and/or within the operating system 822.

The memory 806 also stores multiple connection interval schemes 830 for managing the BLE link between the EI and IMD. The memory 806 may store connection criteria (e.g., thresholds) with or separate from the CI schemes 830. The processor 804, under the control of the IMD application 824, directs the RF circuit 802 to change the BLE connection interval according to data throughput requirements or BLE signal quality based on the BLE dynamic connection interval scheme 830.

The foregoing discussion has been in connection with IMDs operating in an advertising state, while EIs operate in a scanning state, while connected via a BLE link. Optionally, the foregoing operations may be reversed, such that IMDs operate in a scanning state, while external devices operate in an advertising state. When the transmitting and scanning operations are reversed, the IMD implements the scanning operations in accordance with a corresponding scanning schedule as described herein. The external instrument implements advertising operations in accordance with a corresponding advertising schedule as described herein.

Closing

It should be clearly understood that the various arrangements and processes broadly described and illustrated with respect to the Figures, and/or one or more individual components or elements of such arrangements and/or one or more process operations associated of such processes, can be employed independently from or together with one or more other components, elements and/or process operations described and illustrated herein. Accordingly, while various arrangements and processes are broadly contemplated, described and illustrated herein, it should be understood that they are provided merely in illustrative and non-restrictive fashion, and furthermore can be regarded as but mere examples of possible working environments in which one or more arrangements or processes may function or operate.

As will be appreciated by one skilled in the art, various aspects may be embodied as a system, method or computer (device) program product. Accordingly, aspects may take the form of an entirely hardware embodiment or an embodiment including hardware and software that may all generally be referred to herein as a "circuit," "module" or "system." Furthermore, aspects may take the form of a computer (device) program product embodied in one or more computer (device) readable storage medium(s) having computer (device) readable program code embodied thereon.

Any combination of one or more non-signal computer (device) readable medium(s) may be utilized. The non-signal medium may be a storage medium. A storage medium may be, for example, an electronic, magnetic, optical, electromagnetic, infrared, or semiconductor system, apparatus, or device, or any suitable combination of the foregoing. More specific examples of a storage medium would include the following: a portable computer diskette, a hard disk, a random access memory (RAM), a dynamic random access memory (DRAM), a read-only memory (ROM), an erasable programmable read-only memory (EPROM or Flash memory), a portable compact disc read-only memory (CD-ROM), an optical storage device, a magnetic storage device, or any suitable combination of the foregoing.

Program code for carrying out operations may be written in any combination of one or more programming languages. The program code may execute entirely on a single device, partly on a single device, as a stand-alone software package, partly on single device and partly on another device, or entirely on the other device. In some cases, the devices may be connected through any type of network, including a local area network (LAN) or a wide area network (WAN), or the connection may be made through other devices (for example, through the Internet using an Internet Service Provider) or through a hard wire connection, such as over a USB connection. For example, a server having a first processor, a network interface, and a storage device for storing code may store the program code for carrying out the operations and provide this code through its network interface via a network to a second device having a second processor for execution of the code on the second device.

Aspects are described herein with reference to the figures, which illustrate example methods, devices and program products according to various example embodiments. These program instructions may be provided to a processor of a general purpose computer, special purpose computer, or other programmable data processing device or information handling device to produce a machine, such that the instructions, which execute via a processor of the device implement the functions/acts specified. The program instructions may also be stored in a device readable medium that can direct a device to function in a particular manner, such that the instructions stored in the device readable medium produce an article of manufacture including instructions which implement the function/act specified. The program instructions may also be loaded onto a device to cause a series of operational steps to be performed on the device to produce a device implemented process such that the instructions which execute on the device provide processes for implementing the functions/acts specified.

The units/modules/applications herein may include any processor-based or microprocessor-based system including systems using microcontrollers, reduced instruction set computers (RISC), application specific integrated circuits (ASICs), field-programmable gate arrays (FPGAs), logic circuits, and any other circuit or processor capable of executing the functions described herein. Additionally or alternatively, the modules/controllers herein may represent circuit modules that may be implemented as hardware with associated instructions (for example, software stored on a tangible and non-transitory computer readable storage medium, such as a computer hard drive, ROM, RAM, or the like) that perform the operations described herein. The above examples are exemplary only, and are thus not intended to limit in any way the definition and/or meaning of the term "controller." The units/modules/applications herein may execute a set of instructions that are stored in one or more storage elements, in order to process data. The storage elements may also store data or other information as desired or needed. The storage element may be in the form of an information source or a physical memory element within the modules/controllers herein. The set of instructions may include various commands that instruct the modules/applications herein to perform specific operations such as the methods and processes of the various embodiments of the subject matter described herein. The set of instructions may be in the form of a software program. The software may be in various forms such as system software or application software. Further, the software may be in the form of a collection of separate programs or modules, a program module within a larger program or a portion of a program module. The software also may include modular programming in the form of object-oriented programming. The processing of input data by the processing machine may be in response to user commands, or in response to results of previous processing, or in response to a request made by another processing machine.

It is to be understood that the subject matter described herein is not limited in its application to the details of construction and the arrangement of components set forth in the description herein or illustrated in the drawings hereof. The subject matter described herein is capable of other embodiments and of being practiced or of being carried out in various ways. Also, it is to be understood that the phraseology and terminology used herein is for the purpose of description and should not be regarded as limiting. The use of "including," "comprising," or "having" and variations thereof herein is meant to encompass the items listed thereafter and equivalents thereof as well as additional items.

It is to be understood that the above description is intended to be illustrative, and not restrictive. For example, the above-described embodiments (and/or aspects thereof) may be used in combination with each other. In addition, many modifications may be made to adapt a particular situation or material to the teachings herein without departing from its scope. While the dimensions, types of materials and coatings described herein are intended to define various parameters, they are by no means limiting and are illustrative in nature. Many other embodiments will be apparent to those of skill in the art upon reviewing the above description. The scope of the embodiments should, therefore, be determined with reference to the appended claims, along with the full scope of equivalents to which such claims are entitled. In the appended claims, the terms "including" and "in which" are used as the plain-English equivalents of the respective terms "comprising" and "wherein." Moreover, in the following claims, the terms "first," "second," and "third," etc. are used merely as labels, and are not intended to impose numerical requirements on their objects or order of execution on their acts.

What is claimed is:

1. A method, comprising:
   initiating a communication link between an external instrument (EI) and an implantable medical device (IMD);
   establishing a first connection interval for conveying data packets between the EI and IMD;
   monitoring a connection criteria that includes at least one of a data throughput requirement, a battery indicator or link condition of the communications link between the IMD and EI; and
   changing from the first connection interval to a second connection interval based on the connection criteria, wherein the second connection interval is longer than the first connection interval, the changing operation comprising changing to the second connection interval when the data throughput requirement drops below a data threshold.

2. The method of claim 1, wherein the changing operation dynamically changes between the first and second connection intervals based on the data throughput requirements.

3. The method of claim 1, wherein the changing operation dynamically changes between the first and second connection intervals based on the link condition of the communications link.

4. A method, comprising:
   initiating a communication link between an external instrument (EI) and an implantable medical device (IMD);
   establishing a first connection interval for conveying data packets between the EI and IMD;
   monitoring a connection criteria that includes at least one of a data throughput requirement, a battery indicator or link condition of the communications link between the IMD and EI; and
   changing from the first connection interval to a second connection interval based on the connection criteria, wherein the first connection interval is shorter than the second connection interval, the method further comprising changing from the second connection interval back to the first connection interval when the link condition drops below a quality threshold.

5. The method of claim 4, wherein the changing operation dynamically changes between the first and second connection intervals based on the data throughput requirements.

6. The method of claim 4, wherein the changing operation dynamically changes between the first and second connection intervals based on the link condition of the communications link.

7. A method, comprising:
   initiating a communication link between an external instrument (EI) and an implantable medical device (IMD);
   establishing a first connection interval for conveying data packets between the EI and IMD;
   monitoring a connection criteria that includes at least one of a data throughput requirement, a battery indicator or link condition of the communications link between the IMD and EI;
   changing from the first connection interval to a second connection interval based on the connection criteria;

initially uploading device configuration information from the IMD to the EI utilizing the first connection interval; and conveying control commands between the IMD and EI utilizing the second connection interval.

8. The method of claim 7, wherein the changing operation dynamically changes between the first and second connection intervals based on the data throughput requirements.

9. The method of claim 7, wherein the changing operation dynamically changes between the first and second connection intervals based on the link condition of the communications link.

10. A method, comprising:

initiating a communication link between an external instrument (EI) and an implantable medical device (IMD);

establishing a first connection interval for conveying data packets between the EI and IMD;

monitoring a connection criteria that includes at least one of a data throughput requirement, a battery indicator or link condition of the communications link between the IMD and EI; and changing from the first connection interval to a second connection interval based on the connection criteria, wherein the changing operation further comprises conveying an interval command from the EI to the IMD directing the IMD to change to the second connection interval.

11. The method of claim 10, wherein the changing operation dynamically changes between the first and second connection intervals based on the data throughput requirements.

12. The method of claim 10, wherein the changing operation dynamically changes between the first and second connection intervals based on the link condition of the communications link.

13. A method, comprising:

initiating a communication link between an external instrument (EI) and an implantable medical device (IMD);

establishing a first connection interval for conveying data packets between the EI and IMD;

monitoring a connection criteria that includes at least one of a data throughput requirement, a battery indicator or link condition of the communications link between the IMD and EI; and changing from the first connection interval to a second connection interval based on the connection criteria, wherein the changing operation further comprises selecting one of the first and second connection intervals to maintain a current drain on a battery of the IMD within a predetermined current drain limit.

14. The method of claim 13, wherein the changing operation dynamically changes between the first and second connection intervals based on the data throughput requirements.

15. The method of claim 13, wherein the changing operation dynamically changes between the first and second connection intervals based on the link condition of the communications link.

* * * * *